US010641764B2

(12) United States Patent
Holden et al.

(10) Patent No.: US 10,641,764 B2
(45) Date of Patent: May 5, 2020

(54) MEMBRANE AND DROPLET-INTERFACE BILAYER SYSTEMS AND METHODS

(71) Applicant: The University of Massachusetts, Boston, MA (US)

(72) Inventors: Matthew A. Holden, Amherst, MA (US); Max J. Lein, Belmont, MA (US); Arash Manafirad, Amherst, MA (US); Dan Ezra Aurian-Blajeni, Newport, RI (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 15/741,103

(22) PCT Filed: Jul. 1, 2016

(86) PCT No.: PCT/US2016/040665
§ 371 (c)(1),
(2) Date: Dec. 29, 2017

(87) PCT Pub. No.: WO2017/004504
PCT Pub. Date: Jan. 5, 2017

(65) Prior Publication Data
US 2018/0196040 A1    Jul. 12, 2018

Related U.S. Application Data

(60) Provisional application No. 62/187,951, filed on Jul. 2, 2015.

(51) Int. Cl.
*G01N 33/543*    (2006.01)
*G01N 33/68*    (2006.01)
*B01J 13/08*    (2006.01)

(52) U.S. Cl.
CPC .......... *G01N 33/5432* (2013.01); *B01J 13/08* (2013.01); *G01N 33/6872* (2013.01); *G01N 2500/20* (2013.01)

(58) Field of Classification Search
None
See application file for complete search history.

(56) References Cited

U.S. PATENT DOCUMENTS 6,723,814 B2    4/2004  Meier et al.
8,268,627 B2    9/2012  Baylery et al.
(Continued)

FOREIGN PATENT DOCUMENTS

WO    200142782     6/2001
WO    2009024775    2/2009
(Continued)

OTHER PUBLICATIONS

Bayley, Hagan, et al., "Droplet interface bilayers", Mol Biosyst. Dec. 2008; 4(12), pp. 1191-1208.
(Continued)

*Primary Examiner* — Bradley R Spies
(74) *Attorney, Agent, or Firm* — Cantor Colburn LLP

(57) ABSTRACT

Droplet-interface bilayer and lipid bilayer membrane compositions stabilized with an amphiphilic polymer are disclosed. Methods of making and using the compositions are also disclosed.

10 Claims, 8 Drawing Sheets

(56) References Cited

U.S. PATENT DOCUMENTS

| | | | | |
|---|---|---|---|---|
| 2011/0177498 A1* | 7/2011 | Clarke | ............... | C07K 14/245 435/6.1 |
| 2011/0229877 A1* | 9/2011 | Jayasinghe | ............ | C12N 9/127 435/6.1 |
| 2015/0285781 A1* | 10/2015 | Heron | ............... | B01D 69/122 436/89 |

FOREIGN PATENT DOCUMENTS

| | | | | |
|---|---|---|---|---|
| WO | 2009077734 | | 6/2009 | |
| WO | WO-2010004265 A1 | * | 1/2010 | ............ C12N 9/127 |
| WO | WO-2010004273 A1 | * | 1/2010 | ............ C07K 14/245 |
| WO | 2010034018 A2 | | 3/2010 | |
| WO | 2013064837 A1 | | 5/2013 | |
| WO | 2014064444 | | 5/2014 | |
| WO | 2014064461 | | 5/2014 | |
| WO | 2016034591 | | 3/2016 | |

OTHER PUBLICATIONS

Ho, K.Y. et al., "Engineering artificial cells by combining HeLa-based cell-free expression and ultra-thin double emulsion template", Methods Cell Biol 2015; 128: pp. 303-318.

Holden, M. et al., "Functional Bionetworks from Nanoliter Water Droplets", J. Am. Chem. Soc. 2007, 129; pp. 8650-8655.

Huang, Jing, et al., "Direct Quantitation of Peptide-Mediated Protein Transport across a Droplet-interface Bilayer", J. Am. Chem. Soc. 2011, 133; pp. 1818-15821.

International Search Report for International Application No. PCT/US2016/040665; International Filing Date: Jul. 1, 2016; dated Sep. 30, 2016; 6 pages.

Lein, Max J, "Droplet-Interface Bilayer Technologies for Membrane Protein Analysis and Molecular Trafficking Measurements" (2013). Doctoral Dissertation, University of Massachusetts.

Portonovo, S. A. et al., "hERG drug response measured in droplet bilayers", Biomed Microdevices 2013, 15 (2); pp. 255-259 (published online: Nov. 18, 2012).

Schlict, B et al., "Droplet-interface-bilayer assys in microfluidic passive networks", Scientific Reports vol. 5:9951; Apr. 2015; DOI:10.1038/srep09951; (8 pages).

Syeda, R. et al.,"Screening Blockers against a Potassium Channel with a Droplet Interface Bilayer Array", J. Am. Chem.Soc. 2008, 130; pp. 15543-15548.

Written Opinion of the International Searching Authority for International Application No. PCT/US2016/040665; International Filing Date: Jul. 1, 2016; dated Sep. 30, 2016; 6 pages.

* cited by examiner

MEMBRANE AND DROPLET-INTERFACE BILAYER SYSTEMS AND METHODS

CROSS REFERENCE TO RELATED APPLICATIONS

This application is a National Stage application of PCT/US2016/040665, filed Jul. 1, 2016, which claims priority to U.S. application No. 62/187,951, filed Jul. 2, 2015, the disclosure of each of which is incorporated herein by reference in its entirety.

BACKGROUND

Screening novel small molecule drugs against human ion channels is of utmost importance in ensuring the safety and efficacy of 21st century therapeutics. Ligand and voltage-gated ion channels making up more than 15% of FDA-approved drug targets, Unwanted blockage or stimulation of ion channels by drugs has caused severe side effects and deaths. Several blockbuster drugs were pulled from the market because of these side effects. There are at least two reasons to be concerned with this problem. First, patients cannot be guaranteed their safety when taking new medicines. Second, not every person is sensitive to these side effects, so they are effectively being denied treatment when a drug is pulled.

Currently, screening ion channels for unwanted drug interactions is an expensive and painstaking process. Though methods based on fluorescent plate readers have accelerated the screening process, electrophysiology is still required to understand how drugs and channels interact. Patch clamp electrophysiology requires live cells and sophisticated instrumentation, and a new cell line must be created for each channel or mutation to be studied. Reconstitution of channel proteins into artificial membranes (lipid bilayers) can be performed, however the purification and reconstitution of membrane proteins into lipid bilayers is an expensive, laborious and difficult practice.

U.S. Pat. No. 8,268,627 discloses a membrane system, the droplet-interface bilayer, as an alternative technology to cell-based methods or planar bilayer methods for study of membrane protein behavior. Briefly, a replica cell membrane is created by joining two independently-formed lipid monolayers together. Two aqueous droplets containing lipid vesicles are submerged under an oily hydrocarbon, typically hexadecane. The lipid vesicles fuse at the oil/water boundary of each droplet to form a self-assembled lipid monolayer around each aqueous droplet. When the two droplets are brought into contact, the hexadecane is squeezed out from between the monolayers to create a droplet-interface bilayer (DIB). Membrane proteins present within one of the aqueous droplets insert into the bilayer. An Ag/AgCl electrode within each droplet enables the application of a voltage and the measurement of ionic current flowing through channels in the DIB.

In vitro transcription and translation (IVTT) is a cell-free approach for the synthesis of proteins from DNA templates. Many IVTT systems and in vitro transcription (IVT) products that synthesize proteins from messenger RNA are now commercially available from a number of vendors and are capable of producing integral membrane proteins such as ion channels.

The cost of producing ion channels via IVTT reactions is relatively high when used with planar bilayer systems, where the aqueous compartment volumes are 100-1000 µL. Droplet-interface bilayers have emerged as a system with greater potential for this application because the required volumes are much lower (e.g., 200 nL per droplet) and the bilayers have higher stability.

Bacterial and viral membrane proteins with both α-helical and β-barrel structures, such as staphylococcal α-hemolysin, the potassium channel Kcv from chlorella virus, and the potassium channel KcsA from *Streptomyces lividans*, have been expressed by IVTT systems derived from *E. coli* and then incorporated in DIBs.

In vitro expression of eukaryotic membrane proteins presents unique challenges. In eukaryotic organisms, synthesis of membrane proteins proceeds in a series of steps that ensure proper folding and orientation. Much of a cell's interior is occupied by a network of membranes called the endoplasmic reticulum (ER). The ER contains a highly-specialized docking site capable of threading secretory proteins or inserting transmembrane protein segments into the lipid membrane. Called the translocon, this complex is believed to guide the channel's insertion such that only one orientation is possible. The insertion of membrane proteins into the ER is coupled to the protein's synthesis at the ribosome. When the first segment of protein emerges from the ribosome, it is bound by another protein complex called the signal recognition particle (SRP). The SRP binds to both the nascent peptide chain and the ribosome, thereby pausing protein synthesis. The ER contains a membrane-bound SRP receptor, which binds the SRP-peptide-ribosome complex. This membrane association effectively docks the ribosome with the translocon. When this occurs, the SRP is released and protein synthesis resumes, with each transmembrane domain threading into the membrane one at a time. For membrane proteins, like ion channels, the first transmembrane α-helix is the binding site for SRP. In short, the ribosome, SRP, SRP receptor, and translocon work together to insert and orient membrane proteins such as ion channels.

In many cases, bacterial IVTT systems are ill-suited for eukaryotic membrane protein expression within the DIB. Bacterial IVTT systems do not post-translationally modify the expressed proteins. More importantly, the translocon is absent from such bacterial systems. To be generally useful for animal or human membrane protein analysis, the IVTT-DIB approach would require all the components that eukaryotic organisms use for membrane protein expression.

To synthesize ion channels within a DIB system, an in vitro transcription/translation (IVTT) extract can be mixed with lipid vesicles and DNA for the desired membrane protein in the aqueous solution of one of the precursor droplets. Including an *E. coli* IVTT system in a DIB, membrane proteins such as the viral potassium channel protein (Kcv,) have been synthesized in situ. Unfortunately, these bilayer interfaces were found to be very unstable, lasting only a couple minutes. DIBs are even less stable when attempting to use any of a variety of eukaryotic expression systems, including rabbit reticulocyte lysate, wheat germ extract, and yeast extract.

There is a need in the art for new compositions and methods for screening ion channel-drug interactions that don't require cells or traditional patch clamping techniques. Further, there is a need in the art for improved cell-free methods to analyze eukaryotic membrane protein function.

SUMMARY

Disclosed herein are compositions for expression and analysis of membrane proteins in a droplet-interface bilayer and lipid bilayer membrane compositions.

In one aspect, a pair of droplets in a hydrophobic medium comprises a first droplet of a first aqueous solution in the hydrophobic medium, the first droplet comprising a layer of amphipathic molecules around the surface of the first aqueous solution, and containing a transcription/translation extract and a heterologous polynucleotide encoding a membrane polypeptide; and a second droplet of a second aqueous solution in the hydrophobic medium, the second droplet comprising a layer of amphipathic molecules around the surface of the second aqueous solution; the first droplet and the second droplet being in contact with one another such that a bilayer of the amphipathic molecules is formed as an interface therebetween; a polymer and optionally the encoded membrane polypeptide are inserted into the bilayer.

In another aspect, a system comprises a bilayer of amphipathic molecules provided at the interface between a first droplet of a first aqueous solution in a hydrophobic medium, the first droplet comprising a layer of amphipathic molecules around the surface of the first aqueous solution, and containing a transcription/translation extract and a heterologous polynucleotide encoding a membrane polypeptide; and a second droplet of a second aqueous solution in the hydrophobic medium, the second droplet comprising a layer of amphipathic molecules around the surface of the second aqueous solution; wherein the bilayer contains a polymer and optionally the encoded membrane polypeptide.

In another aspect, a droplet of aqueous solution in a hydrophobic medium comprises a layer of amphipathic molecules around the surface of the aqueous solution, and containing a transcription/translation extract; and a heterologous polynucleotide encoding a membrane polypeptide and the hydrophobic medium or an aqueous phase containing a polymer capable of insertion into a bilayer of the amphipathic molecules.

In another aspect, a system comprises a membrane separating first and second volumes of aqueous solution, the membrane comprising a lipid bilayer and an ion channel providing a passageway from one side of the membrane to the other, wherein the membrane contains 30% or less by weight of an amphiphilic polymer.

In another aspect, a membrane bilayer composition comprises a membrane comprising a lipid bilayer and an ion channel providing a passageway from one side of the membrane to the other wherein the membrane contains 30% or less by weight of an amphiphilic polymer.

In another aspect, a system comprises a membrane separating first and second volumes of aqueous solution, the membrane comprising a lipid bilayer and an ion channel providing a passageway from one side of the membrane to the other, wherein the first and/or second volumes of aqueous solution comprises a membrane destabilizing agent and wherein the membrane contains an amount of amphiphilic polymer effective for stabilization of the membrane.

In another aspect, a composition comprises a pair of droplets in a hydrophobic medium, the pair of droplets comprises a first droplet of a first aqueous solution in the hydrophobic medium, the first droplet comprising a layer of lipid molecules around the surface of the first aqueous solution; and a second droplet of a second aqueous solution in the hydrophobic medium, the second droplet comprising a layer of lipid molecules around the surface of the second aqueous solution; the first droplet and the second droplet being in contact with one another such that a bilayer of the lipid molecules is formed as an interface therebetween; wherein the bilayer comprises an amount of amphipathic polymer effective for stabilization of the bilayer.

In another aspect, a composition comprises a droplet in a hydrophobic medium containing an aqueous solution and a hydrophilic layer, the droplet comprising a layer of lipid molecules around the surface of the first aqueous solution and the hydrophilic layer comprising a layer of lipid molecules on the surface of the second aqueous solution; the first droplet and the hydrophilic layer being in contact with one another such that a bilayer of the lipid molecules is formed as an interface therebetween; wherein the bilayer contains an amount of amphipathic polymer effective for stabilization of the bilayer.

Methods of making and using the compositions are also disclosed.

In one aspect, a method of forming a DIB system comprising a bilayer of amphiphilic molecules provided at the interface between two droplets, comprises: forming a first droplet of a first aqueous solution in a hydrophobic medium, the first droplet comprising a layer of amphipathic molecules around the surface of the first aqueous solution, and containing a transcription/translation extract; and a heterologous polynucleotide encoding a membrane polypeptide; forming a second droplet of a second aqueous solution in the hydrophobic medium, the second droplet comprising a layer of amphipathic molecules around the surface of the second aqueous solution, bringing the droplets into contact with one another in the hydrophobic medium so that a bilayer of the amphipathic molecules is formed as an interface between the contacting droplets; and incorporating a polymer into the bilayer.

In another aspect, a method of analyzing membrane polypeptide function comprises contacting a test compound with the DIB system or the membrane system disclosed herein; and measuring a detectable signal from the system in the presence and in the absence of the test compound.

These and other embodiments, advantages and features of the invention become clear when detailed description and examples are provided in subsequent sections.

BRIEF DESCRIPTION OF THE DRAWINGS

Referring now to the figures, which are exemplary embodiments, and wherein the like elements are numbered alike:

FIG. 10 shows a time interval of 2 seconds between panels a) and b). A lipid only DIB tends to rupture if a volume greater that 10% of the droplet's volume is added. However, a polymer-stabilized DIB droplet could double in volume by pipette injection without rupturing. This provides the ability to add reagents to a pre-formed DIB which would be useful in many types of tests.

DETAILED DESCRIPTION

Figure 1:
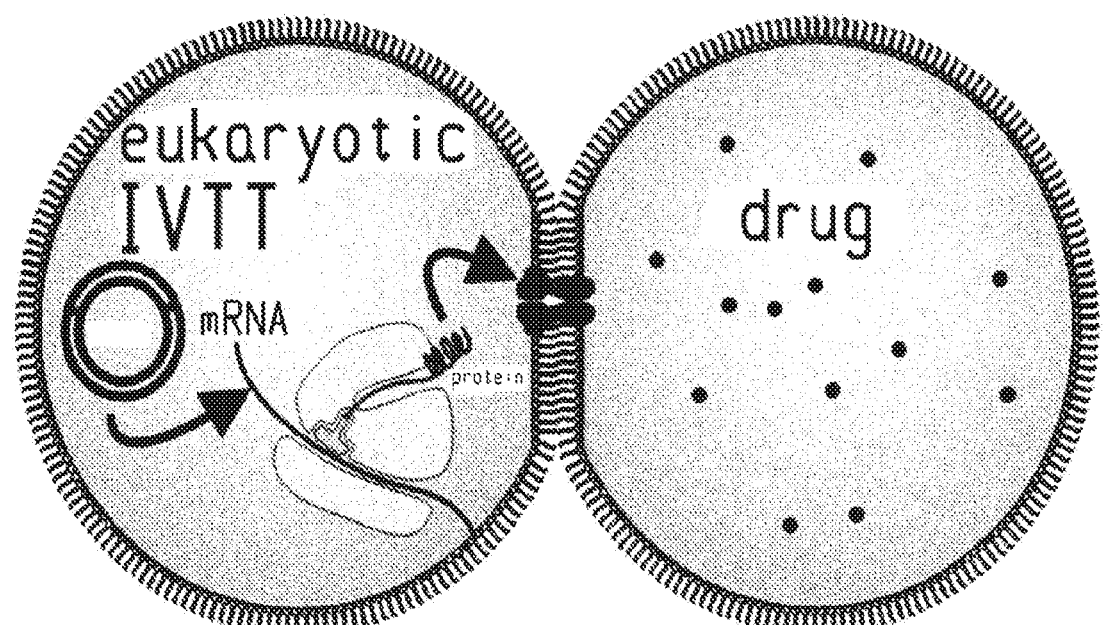
FIG. 1 is a drawing illustrating an exemplary DIB system for coupled in vitro transcription/translation (IVTT)-channel analysis in which the left droplet contains a eukaryotic transcription/translation extract and a plasmid encoding an ion channel gene which is expressed within the droplet by the IVTT system, with subsequent insertion of the ion channel into the bilayer and the right droplet contains molecules of a drug to be tested for its effect on the ion channel.

A stable droplet-interface bilayer (DIB) system for coupled expression and analysis of membrane proteins is disclosed herein. Previous DIB structures for expression of membrane proteins including an in vitro transcription/translation (IVTT) system within one of the droplets were found to be highly destabilized compared to DIBs without the IVTT system, lasting only a few minutes. Complex IVTT extracts may lead to DIB instability for one or more reasons including imbalance of osmotic pressure between the droplets, detergents or other proprietary chemicals added to the matrix, high protein concentrations, or possibly biochemical activity within the matrix.

Further disclosed herein is a membrane system comprising an ion channel that has improved stability. The system may be used in the detection or characterization of an analyte. The system may be used in the delivery of an analyte across the membrane through the ion channel. The system may comprise part of an interconnected droplet network.

The inventors have unexpectedly found that incorporating a small amount of stabilizing amphipathic polymer into the bilayer of an IVTT-containing DIB system stabilizes the DIB for at least 30 minutes without the two droplets coalescing. The disclosed IVTT-containing DIB systems are stable for a sufficiently long time period to permit synthesis of membrane proteins in situ within the IVTT-containing droplet, insertion of the membrane protein into the bilayer of the DIB, and experimental analysis of the protein function. In particular, the disclosed DIB systems permit electrophysiological recordings to detect membrane protein function for extended time periods, producing no current leakage or drift throughout the recording time period. Compositions and methods of making and using the DIB expression/analysis system are disclosed.

Furthermore the inventors have unexpectedly found that the addition of small amounts of amphipathic polymer to a lipid bilayer provides chemical stability and is able to make the lipid bilayer more robust and less susceptible to degradation by destabilizing agents. A lipid bilayer may rupture when exposed to such agents, including certain amphiphiles. Detergents and surfactants, including those commonly used to solubilize membrane proteins, can cause defect formation and bilayer rupture even at relatively low concentrations. Additives used to stabilize cell-derived expression extracts, such as glycerol and polyethylene glycol (PEG), are also known to break DIB membranes. Components of cell-derived expression extracts, including native fatty acids, lipids, proteins and other natural amphiphiles, along with additives, create a milieu that is highly destabilizing to lipid bilayer membranes. High concentrations of detergent-solubilized protein pores also tend to break lipid bilayer membranes such as those in DIBs. However, lipid bilayers containing polymer amphiphiles have been shown to have an increased resistance to rupture when exposed to such destabilizing agents. Thus, amphiphilic polymers such as those that protect DIBs from rupture impart chemical stability to lipid bilayers. The fact that only small amounts of amphipathic polymer were required in order to impart membrane stability was surprising and provides a membrane which has the benefits of both a lipid bilayer membrane and an amphipathic polymer membrane.

The addition of small amounts of amphipathic polymer to a lipid bilayer may also provide mechanical stability. Lipid bilayers are typically sensitive to mechanical perturbation. Increasing the volume of one droplet of a DIB (for example, by injection) may quickly lead to rupture. Furthermore, the application of transmembrane voltages higher than 150 mV typically cause lipid DIB droplets to coalesce. Forces arising from osmotic imbalance, voltage, gravity, fluid flow, and monolayer stretching due to droplet inflation all tend to destroy lipid bilayer membranes. However, when these forces are combined in the presence of a polymer amphiphile-stabilized lipid bilayer membrane such as a DIB, the membrane is stable for at least one hour. For example one droplet of a stabilized DIB could be repeatedly injected with aqueous solution without rupture (see FIG. 10 below) without the need to osmotically balance the droplets. In addition, defects that form in those polymer amphiphile-stabilized DIBs appear to quickly self-heal (see FIG. 3 below). This is not observed in conventional non stabilized lipid bilayer membranes.

In an embodiment the aqueous solutions may contain electrodes to provide a potential difference across the membrane. Charged analytes such as polynucleotides can be induced to translocate the ion channel during which ion current measurements indicative of the analyte may be taken. The aqueous solutions would typically comprise an electrolyte. The electrodes may be reference electrodes such as AgCl. Alternatively the solutions may comprise a suitable redox couple such as ferri/ferrocyanide and the electrodes may be chosen from a relatively inert material such as gold or platinum.

The first and/or second aqueous solutions may comprise an IVTT extract.

In an embodiment the system may further comprise one of more droplets, each droplet comprising a layer of lipid around its surface and forming an interconnected droplet network, wherein a lipid bilayer is formed at each interface between droplets and wherein each lipid bilayer comprises an ion channel. Such suitable systems are disclosed in WO2013/064837 and WO2014/064461, incorporated herein by reference.

Lipid bilayers comprising an ion channel are well known. The lipid bilayer disclosed herein may be prepared for example according to the method of Montal & Mueller (Proc Natl Acad Sci USA. 1972 December; 69(12):3561-6). The lipid bilayer may be formed as a droplet interface bilayer (DIB) or as an interface between a droplet and a planar surface, see for example WO2008/012552 and WO2009/024775 incorporated herein by reference. The may be an interconnected droplet network comprising three or more droplets. The system disclosed herein may be used for example for the delivery of an analyte from one aqueous medium to the other through the ion channel. The analyte may be a drug to be delivered through the ion channel. The system may be used to detect or characterize an analyte, wherein the analyte is caused to translocate the ion channel during which measurements are made, such as the measurement of ion current flow under an applied potential difference, see for example WO2001/42782. The system may comprise an array of membranes for detection of analytes, each membrane comprising an ion channel, such as disclosed by WO2009/077734. The analyte may be a polymer such as a polynucleotide or a polypeptide.

The use of a lipid bilayer membrane to incorporate an ion channel is ideal in many respects in that it mimics the lipid membranes of cell walls in which ion channels may be naturally present. However a drawback of using lipid membranes is that they are fragile and may be subject to degradation which can result in damage to the membrane. Such damage may result in the lowering of the membrane resistance due to the presence of leakage pathways or result in bursting In order to address this problem, non-lipid amphipathic polymer membranes have been developed into which ion channels may be incorporated, such as for example diblock and triblock copolymers. An example of such is poly(dimethylsiloxane)-block-poly(2-methyloxazoline) copolymer. These membranes, being synthetic, are typically more resistant to degradation and have been shown to be more robust than lipid bilayer membranes when subjected to high potential differences. However such membranes do not provide a natural environment for insertion of an ion channel and the addition of a detergent is often necessary in order to facilitate ion channel insertion.

The aqueous solution may for example comprise a biological fluid or a cell extract. The biological fluid may be blood, interstitial fluid, serum, urine, tears, saliva, or plasma. The aqueous solution may be semi-solid or comprise an extract from a solid sample.

Disclosed herein is a droplet-interface bilayer composition.

A droplet-interface bilayer (DIB) may be formed between two droplets wherein each droplet has a layer of amphipathic molecules around its surface.

A droplet-interface bilayer may be formed between a droplet and a hydrophilic layer wherein the droplet has a layer of amphipathic molecules around its surface and the hydrophilic layer has a layer of amphiphilic molecules on its surface. The hydrophilic layer may be provided on a solid support. The hydrophilic layer may be a hydrogel. The hydrophilic layer may be a hydrated support. Suitable examples of such a droplet-interface bilayer are disclosed in WO2009/024775, herein incorporated by reference.

Examples of destabilizing agents that can rupture or provide leakage pathways through otherwise highly resistive lipid bilayers include detergents, surfactants, including those commonly used to solubilize membrane proteins can cause defect formation and bilayer rupture even at relatively low concentrations, additives used to stabilize cell-derived expression extracts such as glycerol and polyethylene glycol (PEG), and components of cell-derived expression extracts, including native fatty acids, lipids, proteins and other natural amphiphiles.

In an embodiment, the composition comprises a pair of droplets in a hydrophobic medium. The pair of droplets comprises a first droplet of a first aqueous solution in the hydrophobic medium, the first droplet comprising a layer of amphipathic molecules around the surface of the first aqueous solution, and containing a transcription/translation extract and a heterologous polynucleotide encoding a membrane polypeptide; and a second droplet of a second aqueous solution in the hydrophobic medium, the second droplet comprising a layer of amphipathic molecules around the surface of the second aqueous solution; the first droplet and the second droplet being in contact with one another such that a bilayer of the amphipathic molecules is formed as an interface therebetween; a polymer and optionally the encoded membrane polypeptide are inserted into the bilayer.

In an embodiment, the composition comprises a system comprising a bilayer of amphipathic molecules provided at the interface between a first droplet of a first aqueous solution in a hydrophobic medium, the first droplet comprising a layer of amphipathic molecules around the surface of the first aqueous solution, and containing a transcription/translation extract and a heterologous polynucleotide encoding a membrane polypeptide; and a second droplet of a second aqueous solution in the hydrophobic medium, the second droplet comprising a layer of amphipathic molecules around the surface of the second aqueous solution; wherein the bilayer contains a polymer and optionally the encoded membrane polypeptide.

In an embodiment, the composition comprises a pair of droplets in a hydrophobic medium. The pair of droplets comprises a first droplet of a first aqueous solution in the hydrophobic medium, the first droplet comprising a layer of lipid molecules around the surface of the first aqueous solution, and containing a lipid bilayer destabilizing agent; and a second droplet of a second aqueous solution in the hydrophobic medium, the second droplet comprising a layer of lipid molecules around the surface of the second aqueous solution; the first droplet and the second droplet being in contact with one another such that a bilayer of the lipid molecules is formed as an interface therebetween; wherein the bilayer comprises an amount of amphipathic polymer effective for stabilization of the bilayer.

In an embodiment, the composition comprises a system comprising a bilayer of lipid molecules provided at the interface between a first droplet of a first aqueous solution in a hydrophobic medium, the first droplet comprising a layer of lipid molecules around the surface of the first aqueous solution, and a second droplet of a second aqueous solution in the hydrophobic medium, the second droplet comprising a layer of lipid molecules around the surface of the second aqueous solution; wherein the bilayer contains an amphipathic polymer at amount of 30% by weight or less of the lipid molecules.

In an embodiment, the composition comprises a droplet in a hydrophobic medium containing an aqueous solution and a hydrophilic layer, the droplet comprising a layer of lipid molecules around the surface of the first aqueous solution and the hydrophilic layer comprising a layer of lipid molecules on the surface of the second aqueous solution; the first droplet and the hydrophilic layer being in contact with one another such that a bilayer of the lipid molecules is formed as an interface therebetween; wherein the bilayer contains an amphipathic polymer.

In an embodiment the aqueous droplet or the hydrophilic layer may comprise a membrane destabilizing agent, in which case the amount of amphipathic polymer. present in the bilayer is sufficient to stabilize the bilayer. The aqueous droplet or the hydrophilic layer may comprise a transcription/translation extract and a heterologous polynucleotide encoding a membrane polypeptide.

The hydrophilic layer may be provided on a solid support. The hydrophilic layer may be a hydrogel. The hydrophilic layer may be a hydrated support. Suitable examples of such a droplet-interface bilayer are disclosed in WO2009/024775, hereby incorporated by reference.

In an embodiment the membrane contains 30% or less by weight of an amphiphilic polymer, such as 25%, 20%, 15% or less.

In an embodiment the membrane contains, between 0.1% and 10% by weight of an amphiphilic polymer, such as 0.2%, 0.5%, 1%, 5%, or more.

In an embodiment the first and/or second volumes of aqueous solution comprise a lipid bilayer destabilizing agent and the membrane or DIB contains an amount of an amphiphilic polymer effective for stabilization.

The first or second volumes of aqueous solution may comprise a transcription/translation extract and a heterologous polynucleotide encoding a membrane polypeptide.

The disclosed compositions, systems, pair of droplets or the droplet-interface bilayer system can be used in assays to analyze expression and/or function of a membrane protein inserted into the bilayer interface between the two droplets.

Also disclosed herein is a droplet of aqueous solution in a hydrophobic medium, the droplet comprising a layer of amphipathic molecules around the surface of the aqueous solution, and containing a transcription/translation extract; and a heterologous polynucleotide encoding a membrane polypeptide and the hydrophobic medium or an aqueous phase containing a polymer capable of insertion into a bilayer of the amphipathic molecules.

The disclosed droplet can be used to prepare a droplet-interface bilayer system for coupled expression and analysis of the encoded membrane polypeptide.

In any of the disclosed compositions, the encoded membrane polypeptide can be a channel or a pore. The encoded membrane polypeptide can be a prokaryotic or eukaryotic polypeptide.

The phrases "in vitro transcription/translation (IVTT)" system and "transcription/translation" system are used interchangeably herein and mean a cell-free system for the synthesis of proteins from DNA templates. Usually, a combination of cell extracts and purified components are combined from multiple sources and optimized to produce either soluble or membrane proteins. Commercially available cell-free protein synthesis systems are typically derived from cell extracts of *Escherichia coli* S30, rabbit reticulocytes, or wheat germ. The drawback of extract-based systems is that they often contain nonspecific nucleases and proteases that adversely affect protein synthesis. Additionally, the first IVTT system formulated from individually purified components from *E. coli* was developed in 2001 and called the "protein synthesis using recombinant elements" or PURE system (Shimizu A et al. Nat Biotechnol 2001, 19:751-755). The transcription/translation system in the disclosed compositions and methods can be a eukaryotic transcription/translation system. In some embodiments, the eukaryotic transcription/translation system comprises a eukaryotic cell extract. A number of eukaryotic cell-free protein expression systems have been derived from yeast, rabbit reticulocytes, wheat germ, insects, and immortalized human cell lines, for example Hela or HEK cells. Eukaryotic IVTT systems are commercially available, e.g., a HeLa IVTT system (ThermoFischerScientific Cat. No. 88882), however noncommercial systems can also be used in the compositions and methods. In some embodiments, the eukaryotic transcription/translation system comprises individually purified components. Supplementation of the eukaryotic transcription/translation system with spherical endoplasmic reticulum fragments called microsomes enables the production of membrane proteins having post-translational modifications such as glycosylation, acetylation, isoprenylation, and phosphorylation.

The formation of a layer of amphipathic molecules around the surfaces of the droplets is straightforward. For example, it may be achieved simply by providing the amphipathic molecules in the hydrophobic medium or in the aqueous solution of the droplets, whereupon the layer can form naturally if the droplets are left for a sufficient period of time. The amphipathic molecules may also be dissolved, or suspended as lipid vesicles in the droplets themselves, from where they again spontaneously form monomolecular layers at the interface between the droplet and the hydrophobic medium, that may have an equilibrating concentration of the amphipathic molecule in the hydrophobic medium.

The bilayer is formed simply by bringing droplets into contact with one another or by bringing into contact a droplet with a hydrophilic surface. The orientation of the amphipathic molecules in the layer around the aqueous solution allows the formation of the bilayer. As the droplets are brought into contact, after the intervening hydrophobic medium has been displaced the bilayer forms very quickly as an interface between the contacting droplets. The bilayer forms a roughly planar surface between the two droplets which are otherwise generally spherical. This planar bilayer is the shape with the lowest free surface energy and has a negative free energy of formation. Formation of the bilayer at the interface of the two droplets is therefore a spontaneous event. The amphipathic molecules allow two droplets to be brought into contact without allowing them to coalesce by the formation of a stable bilayer.

Methods of preparing a droplet-interface bilayer system are disclosed.

The method of forming a system comprising a bilayer of amphiphilic molecules provided at the interface between two droplets can comprise forming a first droplet of a first aqueous solution in the hydrophobic medium, the first droplet comprising a layer of amphipathic molecules around the surface of the first aqueous solution, and containing a transcription/translation extract and a heterologous polynucleotide encoding a membrane polypeptide; forming a second droplet of a second aqueous solution in the hydrophobic medium, the second droplet comprising a layer of amphipathic molecules around the surface of the second aqueous solution; bringing the droplets into contact with one another in the hydrophobic medium so that a bilayer of the amphipathic molecules is formed as an interface between the contacting droplets; and incorporating a polymer into the bilayer. In an embodiment, the hydrophobic medium or an aqueous phase contains a polymer that inserts into the bilayer and incorporating the polymer into the bilayer comprises the polymer self-inserting into the bilayer. In another embodiment, incorporating the polymer into the bilayer comprises contacting the first or the second droplet with a lipid-polymer film on a surface of a substrate in the hydrophobic medium such that a lipid-polymer monolayer forms on a surface of the first or second droplet. Contacting the first or the second droplet with the lipid-polymer film can occur prior to bringing the droplets into contact with one another in the hydrophobic medium. The method can further comprise coating the substrate with a lipid-polymer solution to form the lipid-polymer film on the surface of the substrate.

Bringing droplets into contact with one another can comprise moving one of the droplets into contact with the other droplet. The method can further comprise incubating the first droplet under conditions such that the encoded membrane polypeptide is synthesized and/or incubating the contacted droplets such that the membrane polypeptide is inserted into the bilayer. The droplets can be moved while in contact with one another to vary the area of the bilayer of the amphipathic molecules. The droplets in contact with one another can also be separated.

The droplets may be handled by a variety of techniques. One method of moving the droplets disclosed in U.S. Pat. No. 8,268,627 is to dispose an anchor having a hydrophilic outer surface inside a droplet. Movement of the anchor allows the droplet to be moved, for example to bring it into contact with another droplet. One example of an anchor includes an electrode treated to have a hydrophilic surface to interact with the aqueous droplet.

The formation of the bilayers is highly reversible and repeatable. Droplets which have been brought into contact with one another may be freely separated to divide the bilayer and may be subsequently brought into contact again to re-create the bilayer.

The degree of control makes the formation of the bilayers easy to standardize. In particular, it is easy to vary the area of the bilayer of the amphipathic molecules by moving the droplets when the droplets are in contact with one another. The change in the area of the bilayers may be observed visually or by capacitance measurements. The diameter of the bilayer has been varied over the range from about 30 µm to about 1000 µm, although this is not thought to be the limit.

In addition, the nature of the hydrophobic medium determines the degree of spreading of the contacted monolayers and thereby the contact angle. For example, for bilayers of glycerylmonooleate (GMO) formed in decane as the hydrophobic medium, the contact area is relatively small and the contact angle is about 3°, this being in agreement with contact angles measured in conventional lipid membrane systems. On the other hand, if the hydrophobic medium is squalene, a larger contact area is formed and the contact angle is 25°, again in agreement with measurements on conventional lipid membranes. These solvent-dependent effects reflect the small free energy of formation of the GMO:decane system (around $-4$ mJ/m$^2$) as compared to the GMO:squalene system (around $-500$ mJ/m$^2$), where the bilayer thickness concomitantly decreased from 50 Å to 25 Å, signifying a depletion of the larger squalene solvent from the bilayer. This non-linear increase in free energy of formation departs from simple Lifshitz theory for two infinite slabs of water acting across the thin oil film, and is more in line with a "depletion flocculation" effect. Essentially, the larger squalene solvent molecules are entropically excluded from the GMO bilayer, and this depletion of solvent exerts a greater osmotic pressure on the bilayer, thereby raising the free energy of formation by orders of magnitude in going from decane to squalene, over and above any Lifshitz effects. Adhesion and the strength and stability of the contact then are largely dependent on the presence or absence of solvent in the bilayer.

An advantage of the present composition and methods is that the DIB system allows the use of a relatively small volume of aqueous solution. In particular, the volume may be smaller than that present in the chambers of a cell used in conventional planar bilayer techniques. The droplets may typically have a volume less than about 1000 nL. A droplet disclosed herein can have a volume of at least about 14 pL and less than about 1000 nL, preferably at least about 20 pL and less than about 1000 nL, more preferably at least about 100 nL and less than about 800 nL. In general the droplets may be of any size limited only by the degree of control of the dispenser of the aqueous solution and the limits of optical resolution if direct manipulation is desired. Droplets that are not required to have electrical recording or stimulus from placed electrodes can be assembled in suspension forming a raft or 3D aggregate or flocculent of droplets having dimensions of micrometers to even nanometers that are all in contact with each other via their intervening bilayers. Using a standard pipette, droplets having volumes in the range from 200 nL to 800 nL can be prepared. However, droplets of smaller volumes can be produced with suitable equipment. For example, using micro-pipette manipulation to form droplets from glass micro-pipettes, observed in a relatively powerful microscope, permits formation of droplets of a diameter of about 30 μm and a volume of approximately 14 pL. In suspension, droplet aggregation of droplets of diameter of about 200 nm yields internal volumes of approximately 4 attoliter (aL, i.e., $10^{-18}$ L).

When electrical measurements are to be performed with the droplet, another consideration which can limit desirable droplet size is the need for an electrical interface. The electrodes require a certain amount of surface area in contact with the droplet to permit the flow of electricity through the recording equipment. For example, for an electrode made from a silver wire with a diameter of about 0.1 mm, the droplets have to be bigger than 0.1 mm in diameter. However use of smaller electrodes would allow the droplets to be smaller in diameter. In an embodiment of the compositions and methods disclosed herein, the size of a droplet would be between 100 and 1000 microns in diameter. Such droplets are easy to manipulate but still inexpensive to use.

The polymer incorporated into the interfacial bilayer of the DIB or the membrane bilayer is an amphipathic polymer that can self-assemble into vesicles in dilute solution. Such self-assembling amphipathic polymers can self-direct their insertion into lipid bilayers. The amphipathic polymer can be any amphipathic polymer that does not destabilize the interfacial bilayer formed between the contacted droplets or inhibit biological function of the membrane polypeptide inserted into the interfacial bilayer. The self-assembling amphipathic polymer can be a block copolymer, preferably a linear block copolymer. A "block copolymer" is a copolymer comprising two or more homopolymer subunits linked by covalent bonds. Each structurally unique homopolymer subunit can be designated by a capital letter, such as A or B, to designate a repeating unit in the copolymer. The union of the homopolymer subunits may require an intermediate non-repeating subunit, known as a junction block. Block copolymers with two or three distinct blocks are called diblock copolymers and triblock copolymers, respectively. Examples of suitable block copolymers for use in the disclosed compositions and methods include AB diblock or ABA triblock copolymers. The hydrophobic block can be any hydrophobic polymer that does not result in a block copolymer that destabilizes the interfacial bilayer formed between the contacted droplets or inhibits biological function of the membrane polypeptide inserted into the interfacial bilayer. Examples of suitable hydrophobic block polymers are poly(methyl methacrylate) (PMMA) and silicones. The silicone polymer can be a polydimethylsiloxane. The hydrophilic block can be any hydrophilic polymer that does not result in a block copolymer that destabilizes the interfacial bilayer formed between the contacted droplets or inhibits biological function of the membrane polypeptide inserted into the interfacial bilayer. Examples of suitable hydrophilic polymers are poly(ortho ester), polyethylene glycol (PEG), poly(ε-caprolactone-co-lactide) (PCLA), and poly (2-methyl-2-oxazoline). The polymer can be a tri-block copolymer (ABA) comprising a polydimethylsiloxane (B unit) capped at both ends with a poly(2-methyl-2-oxazoline) (A unit) The length of the polydimethylsiloxane block can be about a 45-mer to a 110-mer, preferably a 50-mer to a 100-mer, more preferably a 55-mer to a 90-mer, yet more preferably a 58-mer to an 80-mer, even more preferably a 60-mer to a 70-mer, and most preferably a 65-mer. The length of a poly (2-methyl-2-oxazoline) capping unit can be about a 2-mer to a 15-mer, preferably a 3-mer to a 12-mer, more preferably a 4-mer to a 10-mer, yet more preferably a 5-mer to an 8-mer, and most preferably a 6-mer. The amphipathic polymer can be purchased commercially or synthesized. Further examples of suitable amphiphilic polymers are disclosed for example in WO2014/064444 and U.S. Pat. No. 6,723,814, hereby incorporated by reference.

The amphipathic polymer can be present in either or both droplets or in the hydrophobic medium. The amphipathic polymer can be present in the droplets or the hydrophobic medium in an amount effective for stabilization of the bilayer of the IVTT-containing DIB. The phrase "amount effective for stabilization" means an amount promoting stabilization of the IVTT-containing DIB such that the DIB is stable for at least 30 minutes without the two droplets coalescing, but does not hinder membrane protein incorporation into the interfacial bilayer of the DIB. For example, when present in the hydrophobic medium, the amphipathic polymer can be at a concentration greater than about 0.01 g/L, greater than about 0.02 g/L, greater than about 0.05 g/L, at least about 0.07 g/L, at least about 0.09 g/L, at least about 0.1 g/L, at least about 0.15 g/mL, at least about 0.2 g/mL or at least about 0.25 g/mL.

The amphipathic polymer can be present in a lipid-polymer film on a surface of a substrate. The amphipathic polymer can be present in the lipid-polymer solution used to make the film at a concentration at least about 0.15 g/mL, at least about 0.2 g/mL or at least about 0.25 g/mL, at least about 0.5 mg/mL.

The lipid-polymer film can be formed on a surface of the substrate by coating the substrate with a lipid-polymer solution. The lipid-polymer solution can be applied by any suitable method. Such methods include pipetting the solution onto the surface followed by evaporation of solvent, spin coating, spray deposition, or stamping. The substrate can be any suitable material that does not dissolve in the solvent or absorb the lipid or polymer, e.g., glass, silicon, or other smooth chemically inert surface, preferably glass, having at least one planar surface.

Alternatively a porous substrate can be used to form the lipid-polymer monolayer on a surface of a droplet. Examples of a porous substrate include alumina and a polymer membrane. Without being bound by theory, it is believed that a porous substrate would serve as a sponge to soak up the lipid-polymer for future deposition to droplets.

In contacting a droplet with the lipid-polymer film on a surface of a substrate in the hydrophobic medium, the droplet can be attached to a support, e.g., an electrode, in the hydrophobic medium. The droplet can be rolled over the film on the substrate surface to transfer a monolayer of lipids and polymer from the film to at least a portion of the monolayer enveloping the droplet. The substrate is submerged in the hydrophobic medium such that the film is presented for contact with a droplet. The film can be presented for contact by placement of the surface at an angle of 25 to 65°, preferably 30 to 60°, more preferably 35 to 55°, yet more preferably 30-50°, most preferably about 45° relative to the surface of the hydrophobic medium. Contacting the droplet with the lipid-polymer film can occur prior to or after bringing the two droplets into contact with one another in the hydrophobic medium.

Lipids in the lipid-polymer solution can comprise any lipids disclosed herein. In an embodiment, the lipid in the lipid-polymer solution can include 1,2-diphytanoyl-sn-glycero-3-phosphocholine (DPhPC), 1,2-diphytanoyl-sn-glycero-3-phosphoethanolamine (DPhPE), or a mixture thereof. In an embodiment, the lipid-polymer solution comprises a mass ratio of 1,2-DPhPC:DPhPE:polymer of 20:5: 0.5 to 20:5:10, preferably 20:5:1 to 20:5:5, most preferably 20:5:1.

Another advantage of the present compositions and methods is that it is possible to bring more than two droplets into contact with each other in a chain or network, for example on a flat or dimpled surface, in a microfluidic channel or, in aggregated or flocculated suspension. The simplicity and control with which the bilayers can be formed simply by moving droplets around makes it straightforward to build large chains or networks which would be impractical in a system where bilayers are formed in apertures in barriers in accordance with conventional techniques. This opens up the possibility of studying much larger systems than is practical with the conventional technique, for example modelling entire systems using multiple droplets.

The droplets and bilayer can be made with a wide range of materials.

In general, the amphipathic molecules can be of any type which form a bilayer in the hydrophobic medium in which the droplets are positioned. This is dependent on the nature of the hydrophobic medium and the aqueous solution, but a wide range of amphipathic molecules are possible. "Amphipathic" molecules are molecules which have both hydrophobic and hydrophilic groups. Herein, "amphipathic" and "amphiphilic" are used synonymously. The layer formed around the droplet is a monolayer of amphipathic molecules which is formed and maintained naturally by the interaction of the hydrophobic and hydrophilic groups with the aqueous solution so that the molecules align on the surface of the droplet with the hydrophilic groups facing inwards and the hydrophobic groups facing outwards.

Examples of amphipathic molecules include hydrocarbon based surfactants and a variety of biological compounds such as phospholipids, cholesterol, glycolipids, fatty acids, bile acids, and saponins. Examples of hydrocarbon based surfactants, include sodium dodecyl sulfate (anionic), benzalkonium chloride (cationic), cocamidopropyl betaine (zwitterionic), and 1-octanol One important class of amphipathic molecules which may be used in forming droplets is lipid molecules. The lipid molecules may be any of the major classes of lipid, including fatty acids, glycerolipids, glycerophospholipids, sphingolipids, sterol lipids, prenol lipids, saccharolipids and polyketides. Some important examples include a phospholipid, a glycolipid and cholesterol. The lipid molecules may be naturally occurring or synthetic.

Lipids forming the lipid bilayer or in the lipid-polymer solution can comprise any suitable lipids. Example lipids include 1,2-diphytanoyl-sn-glycero-3-phosphocholine (DPhPC), 1,2-diphytanoyl-sn-glycero-3-phosphoethanolamine (DPhPE). The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties.

The amphipathic molecules need not be all of the same type. The amphipathic molecules may be mixtures. The monolayer around a given droplet can comprise a single amphipathic molecule or a mixture of amphipathic molecules. Furthermore, the amphipathic molecule or mixture of amphipathic molecules in the respective outer layers of the two droplets brought into contact can be the same or different. For example, the amphipathic molecules in the respective outer layers of the two droplets brought into contact can be of different types or two different mixtures so that the bilayer formed by the two monolayers is asymmetric.

The aqueous solution of each droplet may be freely chosen as appropriate for the experimental study which is to be performed. The first aqueous solution and the second aqueous solution of the two droplets may be the same or different. The nature and concentration of the solutes can be freely varied to vary the properties of the solution. One important property is pH and this can be varied over a wide range. Another important point in experiments using electrical measurements is to select appropriate salts to carry the current. Another important property is osmolarity.

Herein, a "hydrophobic medium" means a water-immiscible solvent. The hydrophobic medium can also be selected from a wide range of materials. The material is hydrophobic so that the aqueous solution forms a droplet rather than mixing with the hydrophobic medium, but otherwise the hydrophobic medium can be freely chosen. The viscosity of the hydrophobic medium can be selected to affect the movement of the droplets and the speed of formation of the layer of amphipathic molecules around the aqueous droplet in the case that they are provided in the hydrophobic medium.

The hydrophobic medium may be an oil. Any type of oil is suitable as long as its surface activity is relatively high, and it does not destabilize the formed bilayer of the contacted droplets. The oil may be a hydrocarbon which may be branched or unbranched, for example a hydrocarbon having from 5 to 20 carbon atoms (although hydrocarbons of lower molecular weight would require control of evaporation). Suitable examples include alkanes or alkenes, such as hexadecane, decane, pentane, or squalene. Other types of oil are also possible. For example the oil may be a silicone or a fluorocarbon. A hydrophobic medium comprising a silicone oil or a fluorocarbon oil might be useful for the study of some systems, for example to minimize loss of a particular membrane protein or analyte from the droplet or to control gas content such as oxygen. The oil can be a single compound or a mixture of compounds.

A membrane polypeptide can be synthesized within the droplet containing the IVTT or provided in one or more of the droplets for insertion into the bilayer. The present method does not limit the choice of membrane polypeptide, provided that the aqueous solution is chosen with appropriate properties for the protein in question. Thus the membrane polypeptide may be of any type. The membrane polypeptide can be a prokaryotic or eukaryotic polypeptide. The membrane polypeptide can be an integral membrane protein or a peripheral membrane protein. The disclosed methods and compositions apply to any membrane proteins including the two major classes that are β-barrels or α-helical bundles. An important application is a membrane polypeptide which is a pore or a channel. Examples of membrane polypeptides include a polypeptide pore or channel, a receptor, a transporter, or a protein which effects cell recognition or a cell-to-cell interaction. In preferred embodiments, the membrane polypeptide is a pore or channel. Suitable pores that may be employed in the system or composition include for example MspA, α-HL, CsgG, lysenin, and homologues and paralogues thereof, such as disclosed in WO2010/0034018 and WO2016/034591. However other pores well known in art may be employed.

The terms "polypeptide," "peptide," and "protein" are used interchangeably herein to refer to a molecule formed from the linking, in a defined order, of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis, or enzymatic synthesis. The terms also apply to amino acid polymers in which one or more amino acid residue is an artificial chemical mimetic of a corresponding naturally occurring amino acid, as well as to naturally occurring amino acid polymers and non-naturally occurring amino acid polymers.

Unless otherwise indicated, a particular polypeptide sequence also implicitly encompasses conservatively modified variants thereof. A conservative amino acid substitution in a polypeptide sequence includes the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLO SUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. One of skill in the art can readily determine regions of the molecule of interest that can tolerate change by reference to Hopp/Woods and Kyte-Doolittle plots.

The term "nucleic acid" or "polynucleotide" includes DNA molecules and RNA molecules. A polynucleotide may be single-stranded or double-stranded. Polynucleotides can contain known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, methyl phosphonates, chiral-methyl phosphonates, 2-O-methyl ribonucleotides, peptide-nucleic acids (PNAs). A polynucleotide can be obtained by a suitable method known in the art, including isolation from natural sources, chemical synthesis, or enzymatic synthesis. Nucleotides may be referred to by their commonly accepted single-letter codes. In preferred embodiments, the polynucleotide encodes a polypeptide, and can be enzymatically transcribed and/or translated.

Unless otherwise indicated, a particular nucleic acid sequence also implicitly encompasses conservatively modified variants thereof (e.g. degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

The IVTT-containing droplet-interface bilayer system can be used to perform experiments involving a process occurring at or through the bilayer of the amphipathic molecules.

A major class of experiments uses a membrane protein inserted into the bilayer. This may be achieved simply by providing the membrane polypeptide in the first or second aqueous solution. The membrane polypeptide can be provided by synthesis within the first droplet by the IVTT system therein. After the formation of the bilayer, the membrane polypeptide naturally inserts into the bilayer in the same manner as with a bilayer formed by conventional techniques.

It has been observed that the bilayer behaves functionally in the same manner as a bilayer formed by conventional techniques. Therefore the bilayer formed by the present methods can be used to perform the same types of experiments, but providing a number of advantages which broaden the range of possible experiments, as discussed further below. Thus the present method may be applied to a wide range of experiments including investigation and/or screening of membrane proteins, investigation and/or screening of analytes which interact with membrane proteins, and investigation and/or screening of the bilayers. Indeed the method may be used to study any bilayer phenomena in general, typically involving a process occurring at or through the bilayer.

Thus, methods of analyzing membrane polypeptide function are disclosed.

The method of analyzing membrane polypeptide function comprises contacting a test compound with the DIB system disclosed herein; and measuring a detectable signal from the system in the presence and in the absence of the test compound. The method can further comprise bringing electrodes into electrical contact with the droplets when the droplets are in contact with one another and measuring an electrical signal using the electrodes.

Measuring a detectable signal from the system can mean measuring an electrical property, measuring a change in an ion concentration, measuring a change in protein conformation, measuring binding of a test compound to the membrane protein, measuring a change in phosphorylation level, measuring a change in second messenger level, measuring a change in neurotransmitter level, measuring a change in a spectroscopic characteristic, measuring a change in a hydrodynamic (e.g., shape) property, measuring a change in a chromatographic property, or measuring a change in solubility. In preferred embodiments, the detectable signal is an electrical signal or a signal from a chromophore.

The test compound can be a small molecule or a biological moiety, such as a protein, a sugar, a nucleic acid, or a lipid.

The following examples are merely illustrative of the compositions and methods disclosed herein and are not intended to limit the scope hereof.

EXAMPLES

Example 1. Preparation of a Stable DIB System Containing a Eukaryotic IVTT Expressing a Membrane Protein In Situ A eukaryotic IVTT containing DIB system is prepared for expressing a human ion channel in situ. A stabilizing polymer is included in the interfacial bilayer of the DIB.

A THERMO SCIENTIFIC 1-Step Human Coupled IVT Kit—DNA (Catalog No. 88882) was used as the IVTT system in the experiments below. This THERMO SCIENTIFIC kit is a mammalian in vitro translation (IVT) system based on HeLa cell lysates. The kit contains all of the cellular components required for protein synthesis, including ribosomes, initiation factors, elongation factors and tRNA. When supplemented with the proprietary accessory proteins and reaction mix included in the kit and with a DNA template, this IVTT system can synthesize protein from the DNA template.

First, two Ag/AgCl electrodes were prepared from 2 cm lengths of 100 μm diameter silver wire. Each wire was briefly melted over a flame to create an approximately 250 μm diameter ball at the end. These were immersed in a solution of sodium hypochlorite until the silver turned dark grey, indicating a layer of AgCl had covered the electrode surface. The ball ends of the electrodes were then coated with a layer of low-melt agarose in buffer; this rendered the electrode surfaces hydrophilic and capable of holding aqueous droplets. Each electrode was fixed by an alligator clip, which in turn was attached to an NMN-21 3-axis micromanipulator (Narishige).

The electrodes were submerged in a homemade acrylic plastic cup-shaped chip filled with hexadecane containing 0.1 mg/mL of 6-65-6 polydimethylsiloxane (PDMS) polymer. IVTT and lipid vesicles were mixed in varying proportions and then 200 nL droplets were manually pipetted onto the grounded (cis) electrode in most cases. Lipid vesicles were usually placed on the opposing (trans) electrode by manually pipetting droplets onto the electrode. The presence of fully formed lipid monolayers was confirmed visually using a stereomicroscope: the droplets droop from the electrodes following monolayer acquisition. After fixing the IVTT droplet to the cis electrode, the electrode was guided via micromanipulator through the chip to form a DIB with the lipid vesicle droplet. The formation of the DIB was monitored by a capacitance measurement and generally occurred within less than a minute after contacting the droplets. The DIB normally increased in size to greater than 300 pF; the droplets were then moved apart slightly to adjust the bilayer size to 300 pF. If a DIB did not form after 5-10 minutes, an applied potential of >100 mV was used to stimulate bilayer formation.

The THERMO SCIENTIFIC kit reagents are thawed on ice 15 minutes before the experiment starts. Meanwhile the coated electrodes are balanced by the vesicle-only solution. The IVTT solution is prepared through hierarchical addition of 5 μL HeLa cell lysate, 1 μL accessory proteins, 0.8 μL hERG channel-expressing plasmid (Genscript) and 2 μL reaction mix, respectively, to a nuclease-free microtube. After about two minutes, 3.8 μL solution of 4 mM lipid vesicles (at a 4:1 ratio of 1,2-diphytanoyl-sn-glycero-3-phosphocholine (DPhPC) to 1,2-diphytanoyl-sn-glycero-3-phosphoethanolamine (DPhPE) in B1 buffer (120 mM KCl, 60 mM NaCl, 10 mM $MgCl_2$ and 10 mM HEPES) is added to the IVTT solution. The solution in the microtube is gently mixed by hand to avoid formation of air bubbles. The final solution incubates for three minutes at room temperature. Then 0.20 μL of the prepared IVTT solution is injected onto the trans-electrode and a 0.20-μL vesicle-only solution of 2 mM lipid vesicle (4:1 DPhPC to DPhPE ratio) in B1 buffer is injected onto the cis-electrode. Taking into account the required relaxation time, on average the droplets are hanging between 3-4 minutes in the oil phase, followed by gentle touching of the two aqueous droplets using mechanical micromanipulators as previously described in Holden M. A. et al. (*J. Am. Chem. Soc.* 2007, 129(27): 8650-8655). The volume percent of the IVTT droplet is composed of 70% IVTT solution and 30% vesicle solution of 4 mM lipid concentration (with 4:1 DPhPC to DPhPE ratio) containing B1 buffer.

After 8-10 minutes of in situ expression of the channel Kv11.1, (encoded by hERG gene) in the DIB, electrophysiological analysis of channel activity is begun. The electrodes are connected to a patch-clamp amplifier (Axopatch 200B; Molecular Devices LLC Axon Instruments) for measurement of ion channel currents, which are digitized with a Digidata 1442A (Molecular Devices LLC) at a sampling rate of 20 kHz. The data from the original recording are digitally lowpass filtered at 200 Hz. The oil reservoir and amplifying headstage are enclosed in a metal box, which serve as a Faraday cage to reduce noise. After the experiment, the droplets can be separated using the micromanipulators.

Figure 4:
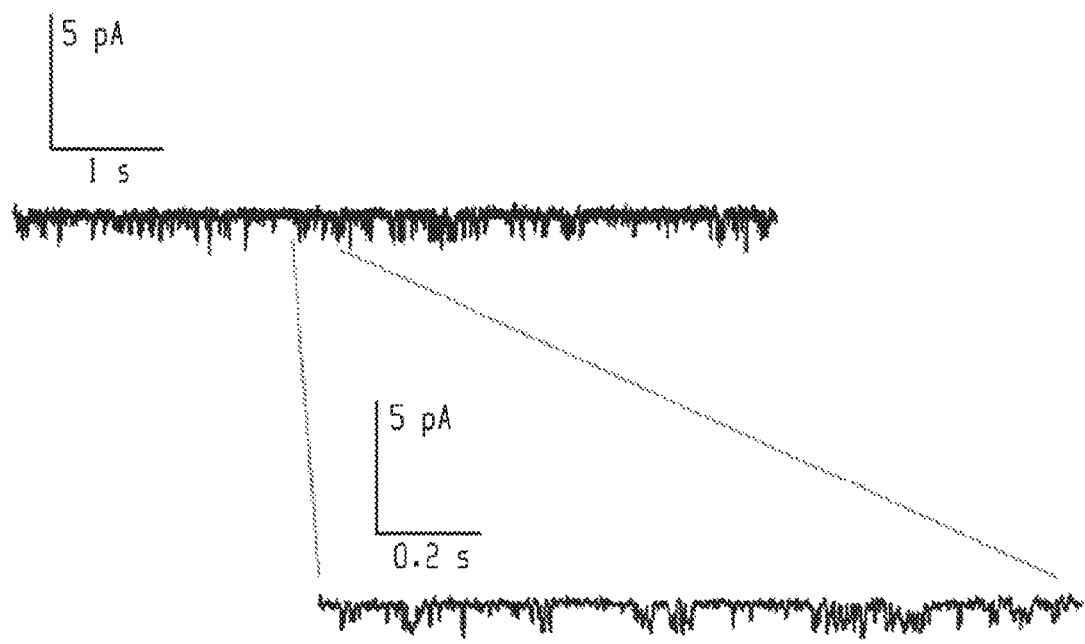
FIG. 4 presents a graph of an electrophysiology recording of activity as a function of time of the human kv11.1 channel (hERG gene) expressed in situ by an IVTT-containing DIB in the presence of a stabilizing polymer. The total recording time for this channel was over 40 minutes.

The results of such an experiment are shown in FIG. 4. The trace shows the activity of a single channel of Kv11.1 at −50 mV in B1 buffer. After channel insertion into the bilayer, channel activity could be observed for more than 40 minutes. The single channel conductance was similar to that observed by others (Portonovo, S. A. et al. *Biomed. Microdevices* 2013, 15 (2), 255-259) and switched between open and closed states (a process known as gating) as expected (Helliwell, R. M. "Recording hERG Potassium Currents and Assessing the Effects of Compounds Using the Whole-Cell Patch-Clamp Technique." *Potassium Channels*. Humana Press, 2009. 279-295.' Vijayvergiya, V. et al. *Biomed. Microdevices* 2015, 17 (1), 12).

Example 2. Preparation of a DIB System Containing a Eukaryotic IVTT and a Membrane Protein in the Presence and Absence of a Stabilizing Polymer Experiments were performed to determine the stability of a DIB containing a eukaryotic cell extract and a stabilizing polymer. In these experiments an IVTT-containing DIB is prepared that includes a pore protein, the toxin α-hemolysin (α-HL), in one droplet for testing the stability of the DIB system in the presence and absence of a stabilizing polymer.

A droplet containing the IVTT was formed by first mixing 70% v/v of an IVTT solution containing 5 μL HeLa cell lysate, 1 μL accessory proteins, 0.8 μL GFP-DNA, and 2 μL reaction mix from a THERMOSCIENTIFIC 1-Step Human Coupled IVT Kit—DNA with 30% v/v of a γ-Cyclodextrin (γCD; Sigma-Aldrich Cat no. C4930)-containing lipid vesicle solution (with a 4:1 DPhPC to DPhPE ratio in B1 buffer). The final γCD concentration in the IVTT droplet is 50 μM and the final lipid vesicle concentration (with 4:1 DPhPC to DPhPE ratio) is 0.8 mM. A second droplet containing 0.2 μg/mL α-hemolysin) and lipid vesicles made from 2 mM of 4:1 DPhPC to DPhPE ratio in buffer (120 mM KCl, 60 mM NaCl, 10 mM $MgCl_2$ and 10 mM HEPES) was then injected to an oil bath containing 0.1 mg/mL of stabilizing polymer. The heptameric hemolysin was provided as a kind gift from Oxford Nanopore Technologies. The stabilizing polymer in this experiment was a triblock copolymer, a 65 mer of polydimethylsiloxane capped at both ends with a 6 mer of poly(2-methyl-2-oxazoline) ("TBCP"; gift from Oxford Nanopore Technologies).

Cyclodextrin acts as a reversible blocker of the α-hemolysin pores. In the experiment, the characteristic binding behavior of cyclodextrin to the α-hemolysin helps to distinguish between conductance through the membrane-inserted toxin α-hemolysin and other pores which might form due to membrane damage.

Figure 2:
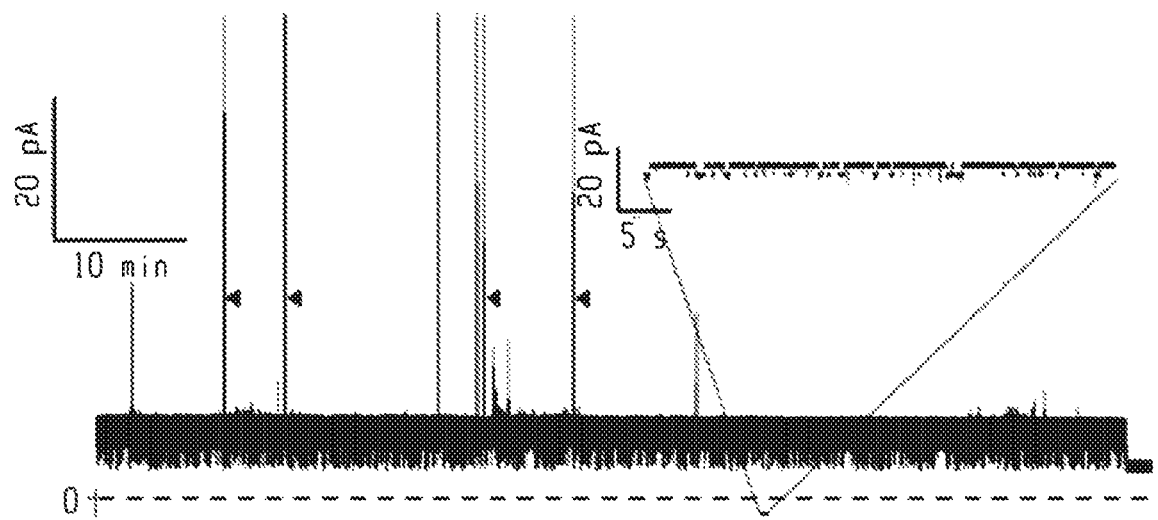
FIG. 2 is a graph of an electrophysiology recording of activity as a function of time of the pore-forming toxin α-hemolysin within a polymer-stabilized DIB containing a eukaryotic cell extract in one droplet and the reversible pore blocker cyclodextrin in the other droplet. The inset shows a small section of the recording (black bar) expanded to show the reversible blockades by cyclodextrin.
Figure 3A:
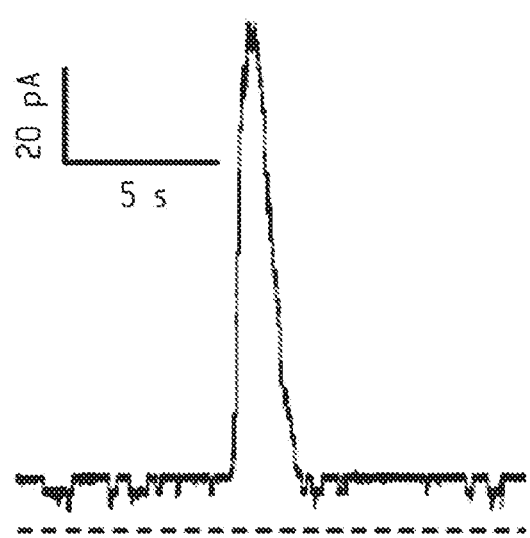
FIGS. 3A, 3B, 3C, and 3D present expanded graphs of regions of FIG. 2 marked with black triangles showing current spikes observed in the polymer-stabilized IVTT-DIBs.
Figure 3B:
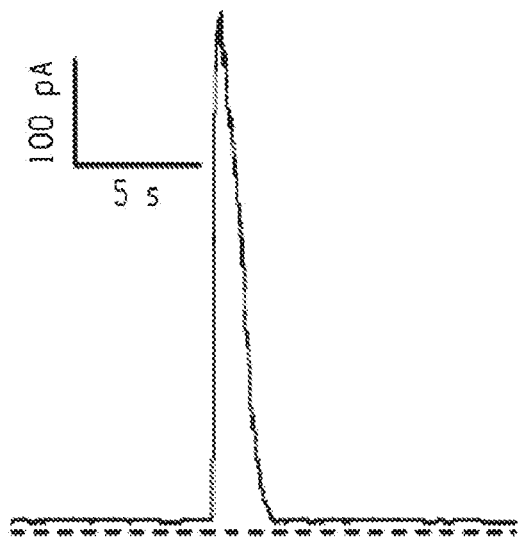
Figure 3C:
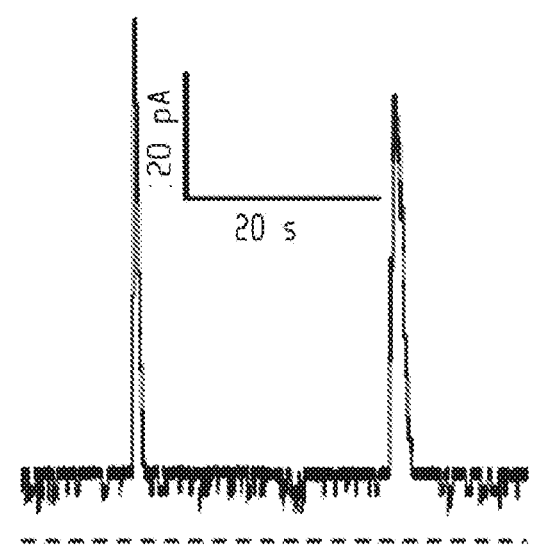
Figure 3D:
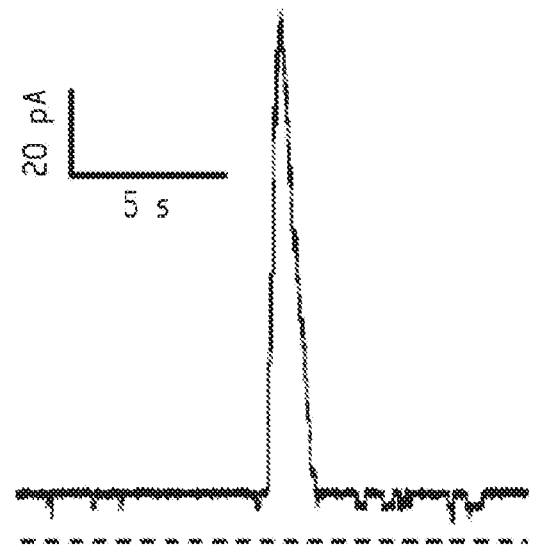

The electrophysiological recording obtained from observing a single α-hemolysin pore for 80 minutes in this IVTT-containing DIB system is shown in FIG. 2. The DIB was stable throughout this time except for brief periods of high conductance (marked by black triangles in FIG. 2). After each spike, the DIB spontaneously returned to a stable baseline and subsequent pore activity was not affected. The inset of FIG. 2 shows a small expanded section of the recording (black bar) to show the α-hemolysin pore blockades by cyclodextrin.

FIGS. 3A, 3B, 3C, 3D present graphs illustrating expanded regions of FIG. 2 marked with black triangles showing current spikes observed in polymer-stabilized IVTT-DIBs. Some spikes are larger than others and all appear to "self-heal" within 5 seconds. Pore blockades by cyclodextrin are observed both before and after each spike, suggesting that the spikes do not affect pore activity.

The toxin α-hemolysin is only able to form conducting ion pores in membranes. If a film thicker than a lipid bilayer was formed in the presence of the amphipathic polymer, no pore activity would be seen. However, in all experiments α-hemolysin activity is observed in the polymer-stabilized DIBs in the presence of the HeLa lysate. For example, a single pore was introduced into a polymer-stabilized IVTT-DIB and its activity was monitored for more than 80 minute (FIG. 2). The magnitude and lifetime of the reversible cyclodextrin blockades of the pore were consistent with previous reports. Therefore, the presence of the polymer does not affect the cyclodextrin-pore interaction.

We noted several interesting features of polymer-stabilized IVTT-DIBs. First, the capacitance of the DIB was far lower in the presence of the polymer. The capacitance of a membrane is directly proportional to its area while inversely proportional to its thickness. As we were routinely able to insert pores into the triblock polymer stabilized DIBs, the thickness of the membrane could only be marginally affected. We attribute the low capacitance to relatively small DIB area.

Second, in most recordings we observed an abrupt end to the pore activity after at least an hour. In the example of FIG. 2, the electrical activity dropped to the baseline current at approximately 80 minutes (FIG. 2, end of recording). One possible explanation is that the polymer may continue to partition into the DIB over time, thickening the membrane to the point where pores cannot be observed. In addition, the surface properties of the droplets change over time, developing a noticeable "shell" that is not seen in the absence of polymer. Creases and wrinkles were seen in the droplets' surface when they were compressed by a pipette tip. These observations suggest that the polymer-droplet interaction evolves over the course of the experiment, changing the properties of the DIB. These changes are unlikely to hinder ion channel-drug interaction studies, since the test would be completed before the membrane would no longer be usable. Specifically, we expect protein synthesis to be completed within 20 minutes, with channel recording immediately following for at most 10 minutes. We were regularly able to record for more than 1 hour of pore activity.

The most striking feature of the polymer-stabilized IVTT-DIB is its ability to self-heal defects. Several large spikes in current were observed during our experiments with the polymer stabilized IVTT-DIBs. Typical examples are highlighted with black triangles in FIG. 2. Upon closer inspection, one can see a rapid rise in current followed by a rapid decrease back to the single-pore current level (FIG. 3). Note that pore blockades by cyclodextrin are observed both before and after each spike, which suggests that the spike does not affect protein activity. The current spikes do not occur in the absence of the IVTT mixture.

Figure 5:
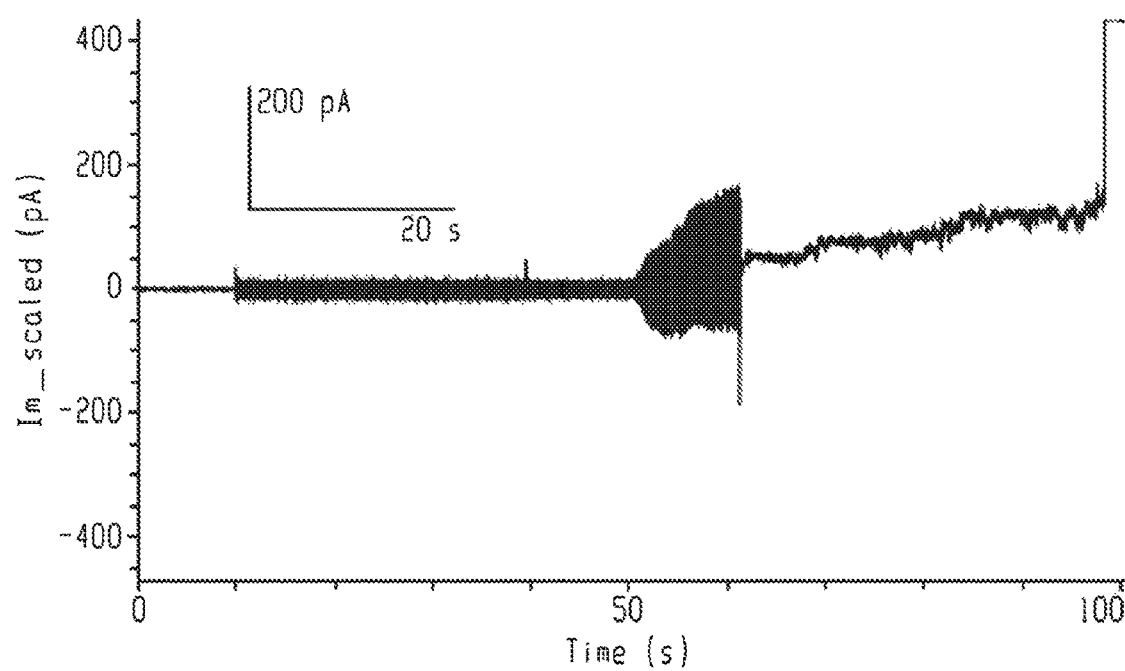
FIG. 5 presents a graph of an electrophysiology recording of toxin (α-hemolysin) activity in a DIB containing a eukaryotic cell extract in the absence of stabilizing polymer. Signals were filtered with a 200 Hz lowpass Bessel filter.

In the absence of the polymer, we were not able to form stable IVTT-DIBs. In experiments in the absence of the polymer, one droplet contained 70% v/v IVTT solution (HeLa lysate, accessory proteins, reaction mixture and GFP-DNA) and 30% v/v aqueous solution of lipid vesicle (4 mM) with γ-cyclodextrin (50 μM) dissolved in B1 buffer while the other droplet contained lipid vesicles (1.3 mM) and α-HL (0.2 m/mL) in B1 buffer. The hydrophobic phase is hexadecane as above, but without the TBCP. IVTT-DIBs formed, but pore activity could be recorded for only brief periods of time in the absence of the polymer. The longest recording we obtained in the absence of the stabilizing polymer was only 100 s. The recording from that experiment is shown in FIG. 5, which shows the recording of the current from the time of initial contact of the two droplets (time 0 s) to the time at which destabilization and coalescence of the drops occurs. Signals were filtered with a 200 Hz lowpass Bessel filter.

Immediately after formation of the DIB, pores insert into the bilayer. As can be seen in FIG. 5, reversible blockages of the pores by cyclodextrin are observed, starting at about 60 sec after droplet contact, but the recording shows that DIB destabilization and coalescence occurs less than a minute later. The trace in FIG. 5 abruptly ends and the current shoots off scale because the droplets coalesce. In comparison to the DIBs including the stabilizing polymer, there are no signs of self-healing in the recording.

Figure 6:
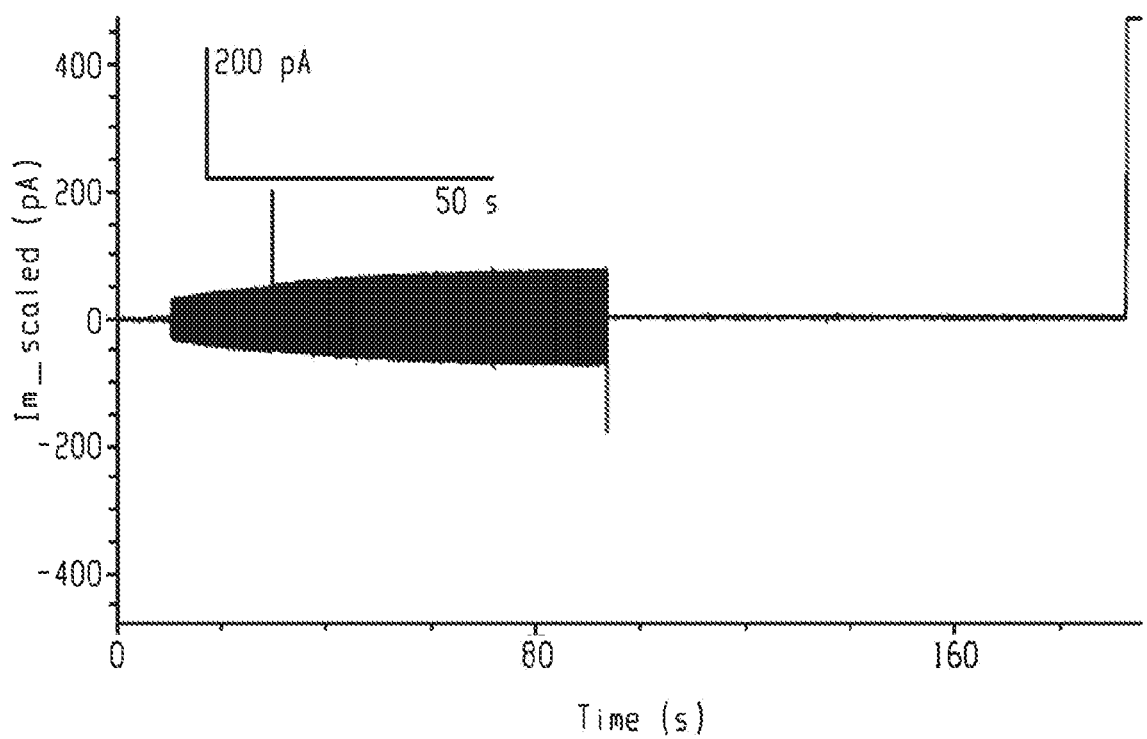
FIG. 6 presents a graph of an electrophysiology recording of a DIB containing a eukaryotic cell extract and α-hemolysin as in FIG. 5, however the droplets of the DIB are equilibrated to a lower temperature (solutions on ice) before injection onto the electrodes. Before incorporation of the toxin, the two aqueous droplets coalescence without any sign of current leakage.

In another control experiment, the IVTT-containing DIB was prepared as above, in the absence of the stabilizing polymer, however in this experiment the two aqueous droplets were injected on the electrodes right after taking the aliquots from ice. Due to the lower initial temperature of the two droplets, it takes a few minutes for the toxin to be incorporated into the bilayer. The electrophysiology recording for this experiment (FIG. 6) shows that before the toxin is incorporated into the bilayer, the bilayer is unstable and the two aqueous droplets coalescence without any sign of current leakage.

Similar membrane instability has been observed using other eukaryotic IVTT systems, including rabbit reticulocyte lysate, wheat germ extract, and yeast extract.

Inclusion of a stabilizing polymer in the bilayer appears to prevent the growth or expansion of membrane defects and may even "plug" defects as they form.

In these experiments to test for DIB stability, the pore protein α-HL was not synthesized in situ. However, a plasmid to express green fluorescent protein (GFP) was included in the IVTT mixture before forming these DIBs to act as a control for IVTT function under the experimental conditions. After each experiment, the fluorescence of the IVTT droplet was measured. In all cases, GFP was expressed. Importantly, neither the presence of the stabilizing amphipathic polymer nor the addition of vesicles and buffering salts affected the IVTT expression of GFP, demonstrating that the conditions required for DIB stability are compatible with the IVTT expression of eukaryotic proteins.

The data suggest that that polymer/lipid interaction may be dynamic, able to self-heal and change over time. Ideally, the polymer would constitute only a small fraction (less than 10%) of the DIB, since the lipids represent the most biomimetic environment for channel analysis.

Figure 7:
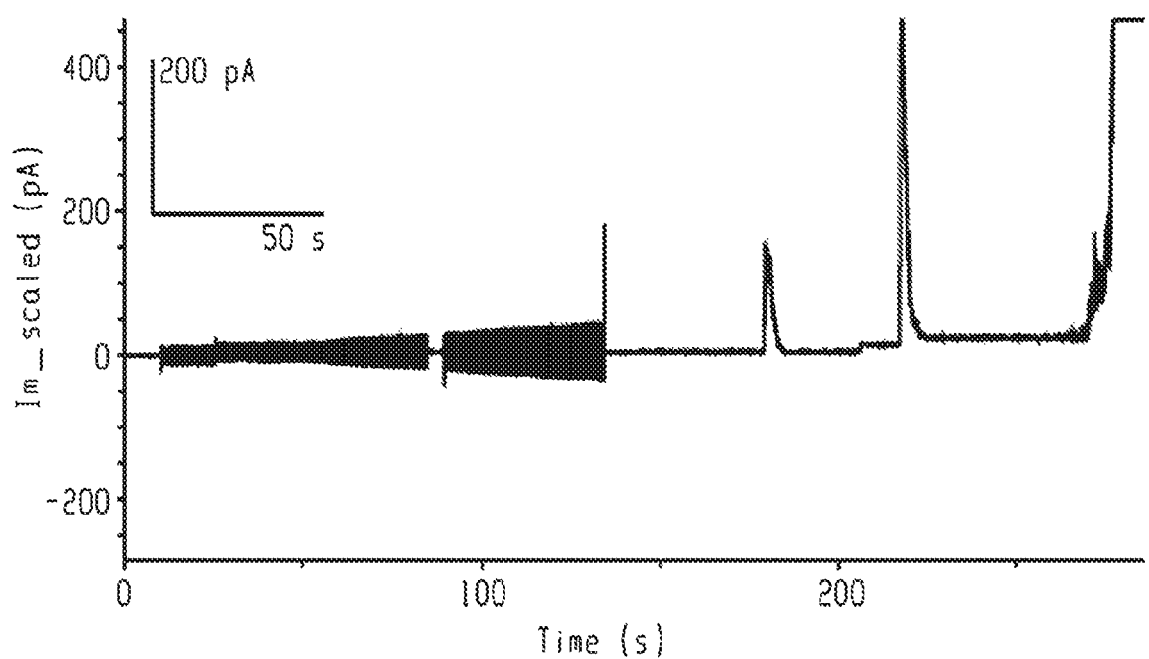
FIG. 7 presents a graph of an electrophysiology recording of a DIB, containing a eukaryotic cell extract and α-hemolysin, formed in a hydrophobic medium containing 0.05 g/L of triblock copolymer dissolved in hexadecane; all other experimental conditions are the same as for the experiment of FIG. 2.

In these experiments, concentrations of less than or equal to 0.05 g/L TBCP in the hexadecane bath did not stabilize the IVTT-DIB. The electrophysiology recording of an experiment including 0.05 g/L TBCP in the hexadecane bath is shown in FIG. 7. All other conditions are identical to those for the experiment of FIG. 2. As can be seen in FIG. 7, two distinct attempts of self-healing happen. Apparently, this amount of polymer is not enough to hold the bilayer together. After the first self-healing attempt, the toxin gets incorporated into DIB (the one-step current increase), however in the absence of enough TBCP molecules the integrity of DIB is compromised.

Example 3. Addition of Polymer by Rolling Method

In order to fix the polymer/lipid ratio at the start of a DIB experiment, we developed a method for adding polymer to the bilayers in which no bulk polymer is dissolved in the hexadecane phase. When including the polymer in the oil bath, the polymer can continue to partition into the DIB during the experiment and will eventually separate the two leaflets. Thus, the membrane changes over time. Without being bound by theory, it is believed that because the rolling method does not include excess polymer in the oil, the initial DIB monolayers remain at a constant polymer/lipid ratio throughout the experiment.

Reagents.

The 1,2-diphytanoyl-sn-glycero-3-phosphocholine (DPhPC) lipid and 1,2-diphytanoyl-sn-glycero-3-phosphoethanolamine (DPhPE) lipid were obtained from Avanti Polar Lipids (Alabaster, AL). Hexadecane and low melting point agarose were obtained from Sigma-Aldrich. The γ-cyclodextrin, silicone oil, sodium chloride, potassium chloride, magnesium chloride and HEPES buffer were obtained from Fisher Scientific. The 1-Step Human Coupled IVT Kit—DNA (Kit Contains HeLa lysate, accessory proteins, reaction mix, positive control DNA: pCFE-GFP and pT7CFE1-CHis) was purchased from ThermoFisher Scientific. Wild Type α-hemolysin pre-heptamer and triblock copolymer (TBCP) were kind gifts from Oxford Nanopore Technologies.

Preparation of Vesicles, Toxin/Blocker Solutions and IVTT Solution.

All vesicles solutions were prepared in B1 buffer (10 mM HEPES, 120 mM KCl, 10 mM MgCl2 and 60 mM NaCl buffered to pH 7.2 with sodium hydroxide). A 4 mM DPhPC:DPhPE (4:1) vesicle solution was prepared by drying an aliquot of DPhPC (in pentane) mixed with DPhPE (in chloroform) dried under a stream of nitrogen until the solvent evaporated, followed by further drying in a vacuum desiccator for 2 hours. Lipids were re-suspended in B1 buffer and extruded once through a polycarbonate filter with 100 nm track-etched pores (Millipore) using a mini-extruder (Avanti). This solution was used to prepare the IVTT-containing droplet.

Final α-hemolysin concentration in the droplet was achieved through serial dilution of a stock solution (20 µg/mL) to 2 µg/mL with 18 MΩ water, followed by a final dilution to the desired concentration to be used in the droplet with B1 buffer. γ-cyclodextrin solution, used as blocker, also was diluted from a stock solution (10 mM) through serial dilution to a final concentration of 500 µM with 18 MΩ water. The last dilution was made with vesicle solution (2 mM, DPhPC: DPhPE) to achieve a final concentration of 50 µM.

Upon receiving the 1-Step Human Coupled IVT Kit, reagents were aliquoted (EPPENDORF LOBIND microcentrifuge tubes) and immediately frozen in liquid nitrogen and stored at −80° C. Each aliquot was prepared to have reagents sufficient for two reactions. The IVTT solution was prepared from the 1-Step Human Coupled IVT Kit—DNA by mixing 5 µL HeLa lysate, 1 µL accessory proteins, 2 µL reaction mix and 0.8 µL pCFE-GFP DNA together after thawing the aliquots of each solution in ice. This solution was used to prepare IVTT-containing droplets containing 70% vol IVTT mixture and 30% vesicle solution (or just B1 buffer in a rolling experiment).

Droplet-Interface Bilayer Formation.

Two Ag/AgCl electrodes were prepared from 2 cm lengths of 100 µm diameter silver wire. Each wire was briefly melted over a flame to create an approximately 250 µm diameter ball at the end. These were then immersed in a solution of sodium hypochlorite until the silver turned dark grey, indicating a layer of AgCl had covered the electrode surface. The ball ends of the electrodes were then coated with a layer of low-melt agarose in buffer (2 wt %); this rendered the electrode surfaces hydrophilic and capable of holding aqueous droplets. Each electrode was fixed by a clip, which in turn was attached to an NMN-21 3-axis micromanipulator (Narishige).

Polymer-Stabilized DIB; Polymer in Oil Bath Method.

The electrodes are submerged in an oil pool (1.2 mL) contained in a homemade acrylic plastic chamber. The composition of the oil is 96% vol hexadecane and 4% vol silicone oil with a final polymer concentration of 0.1 mg/mL. 200 nL droplets of either IVTT-containing complex solution or vesicles are manually pipetted onto the electrodes. Here, the IVTT-containing droplet is composed of 70% vol IVTT mixture (as described above) and 30% vol vesicle solution. The other droplet contained only vesicle solution. In all trials, to examine toxin activity through reversible γ-cyclodextrin block, α-Hemolysin is added to droplets (cis or trans) as part of a vesicle solution with a final concentration of 0.1 µg/mL. Similarly, γ-cyclodextrin is added to droplets (trans or cis) with a final concentration of 50 µM. The electrophysiology conditions are described below.

Polymer-Stabilized DIB; Rolling Approach.

Figure 11:
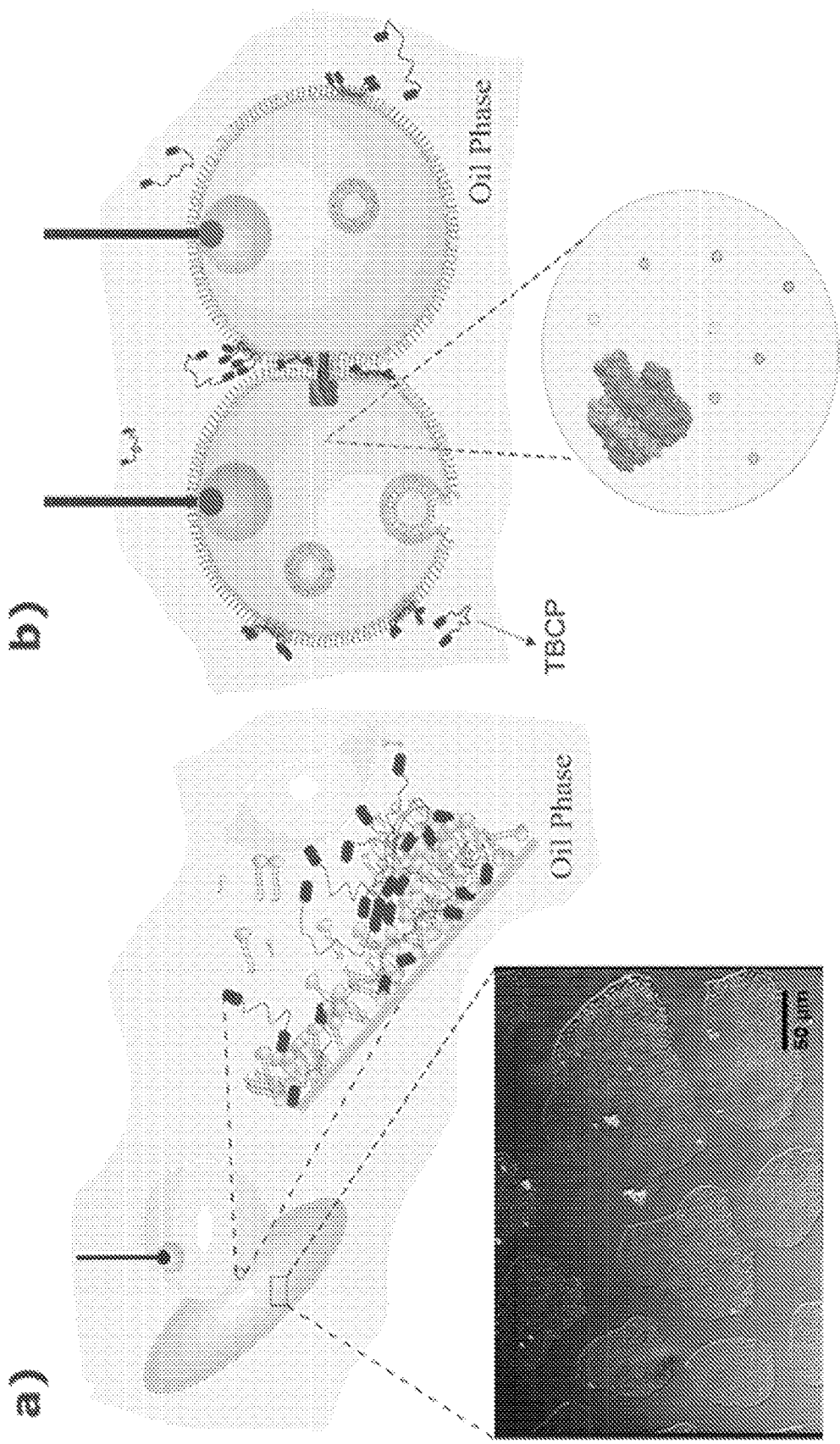
FIG. 11 presents a schematic representation of the two approaches that have been used to prepare a stabilized and robust Droplet Interface Bilayer (DIB) using a tri-block copolymer. Panel (a) is a schematic representation of the rolling approach; in which droplets are rolled (up and down and side-to-side) on a glass slide coated with a polymer-lipid mixture. The photographic inset shows the surface of a coated glass coverslip before insertion into the oil bath. Panel (b) depicts the polymer-in-oil bath approach. Briefly, the working electrode (left) contains buffer solution mixed with a dilute solution of the toxin (shown in the magnified cartoon is the α-hemolysin heptamer, RCSB Protein Data Bank structure 3ANZ). The ground electrode (right) contains buffer solution and a human-derived in vitro transcription/translation (IVTT) extract of HeLa cell lysate with the desired concentration of γ-cyclodextrin used to block the toxin activity.

To restrict the amount of vesicles inside the droplet as a way of inhibiting the unwanted lipid-protein interactions or probable protein sequestering inside lipid vesicles, both cis and trans droplets were prepared without the addition of vesicle solution. B1 buffer was used to prepare both the IVTT-containing droplet (30% vol B1) and the counterpart droplet. In this case, the oil bath was 100% vol hexadecane without the addition of TBCP. The monolayer formation was achieved through rolling of the droplets over a glass coverslip (Fisher Scientific-φ=10 mm) coated with a lipid-polymer film. DPhPC in pentane, DPhPE in chloroform and TBCP in chloroform was mixed together to reach a final mass ratio of 20:5:1 respectively (200 µl DPhPC (10 mg/mL)+50 µl DPhPE (10 mg/mL)+100 µl TBCP (1 mg/mL)). 30 µl of the described solution was carefully placed on the cover slip and without any agitation solvents were evaporated by a nitrogen stream. To remove trace amounts of solvent, the coat was vacuum-dried for 5 hours. After submerging the electrodes (with droplets) into the hexadecane bath, droplets were placed in one side of the chamber and with the aid of a curved tweezer, the cover slip was submerged at about a 45° angle (FIG. 11, panel (a)). In less than 2 minutes both droplets were rolled side-to-side and also up and down to permit monolayer acquisition. After removing the glass slide, droplets were left to relax. With this approach IVTT-containing droplets relaxed much faster (~30 seconds) in comparison to buffer-only droplet.

Electrophysiology.

The electrodes were connected to a patch-clamp amplifier (Axopatch 200B; Axon Instruments). The currents were filtered with a low-pass Bessel filter (200 dB/decade) with a corner frequency of 2 kHz and then digitized with a Digi-Data 1400 series A/D converter (Axon Instruments) at a sampling frequency of 5 kHz. The oil reservoir and amplifying head-stage were enclosed in a metal box, which served as a Faraday cage. In both experimental approaches, the electrodes were guided via micromanipulator to form a DIB with the two droplets. Furthermore, the presence of fully formed lipid monolayers was confirmed visually using a stereomicroscope: the droplets droop (i.e. become relaxed) from the electrodes following monolayer acquisition. The formation of the DIB was monitored by a capacitance measurement and generally occurred within less than a minute after contacting the droplets. For all trials a potential of −70 mV was used unless otherwise mentioned. By convention, the IVTT droplet was always placed on the grounded electrode (cis) and the vesicle droplet was placed on the working electrode (trans). On occasion, a DIB membrane would rupture during experiment, causing the current to jump instantly to an off-scale value. When this occurred, the contaminated electrodes were discarded and replaced with fresh Ag/AgCl electrodes. However, the oil bath was kept and the fused solution was dropped to the bottom of chamber through gentle removal of the electrode from the oil bath. No data was obtained from a ruptured DIB.

Figure 8:
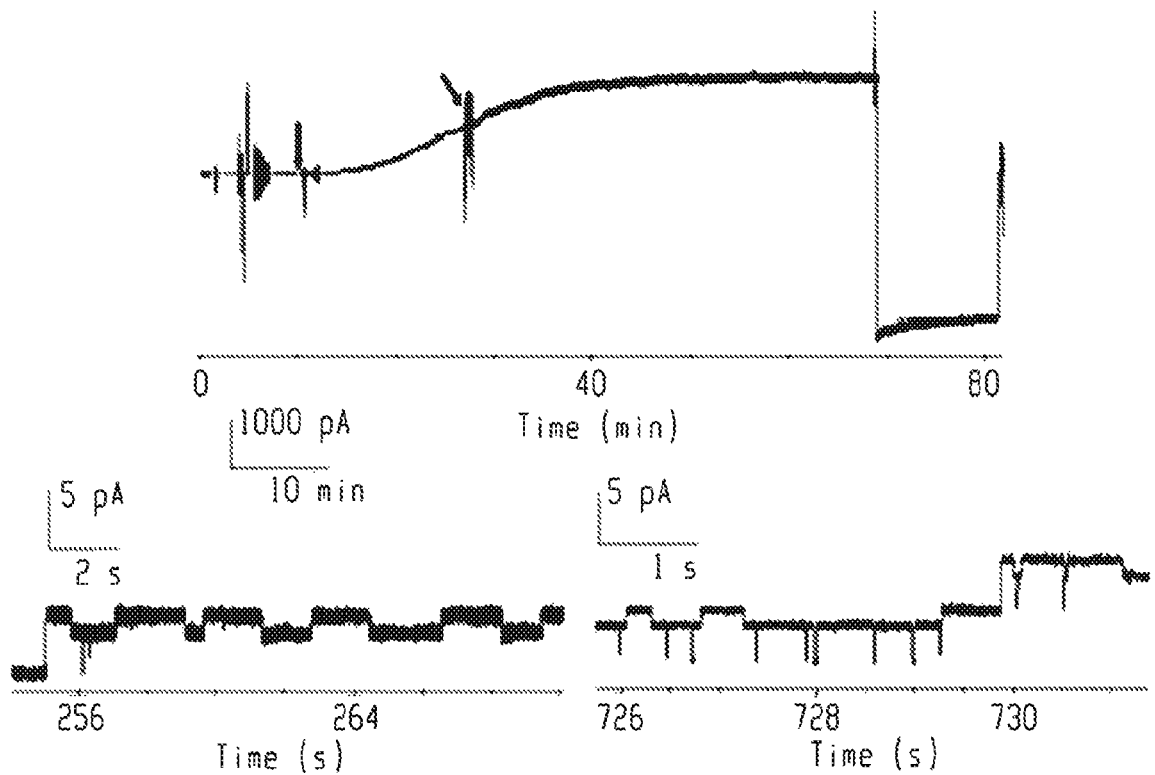
FIG. 8 presents a graph of an electrophysiology recording for a droplet interface bilayer, made by the rolling droplet approach, in the presence of TBCP and a vast number of pores incorporated into the bilayer (α-hemolysin concentration approaching 1 mg/mL). In the early moments only one single pore is active (bottom left), after about 10 minutes other pores are being incorporated (Bottom right). After 10 minutes, droplets were detached to investigate the bilayer reforming (the first arrow). After 27 minutes the presence of bilayer was checked through capacitance (second arrow). From minute 40 to 70 minutes, the current was stable around 1800 pA. After 70 minutes the voltage was switched to –70 mV to check the bilayer stability in both voltages.
Figure 9:
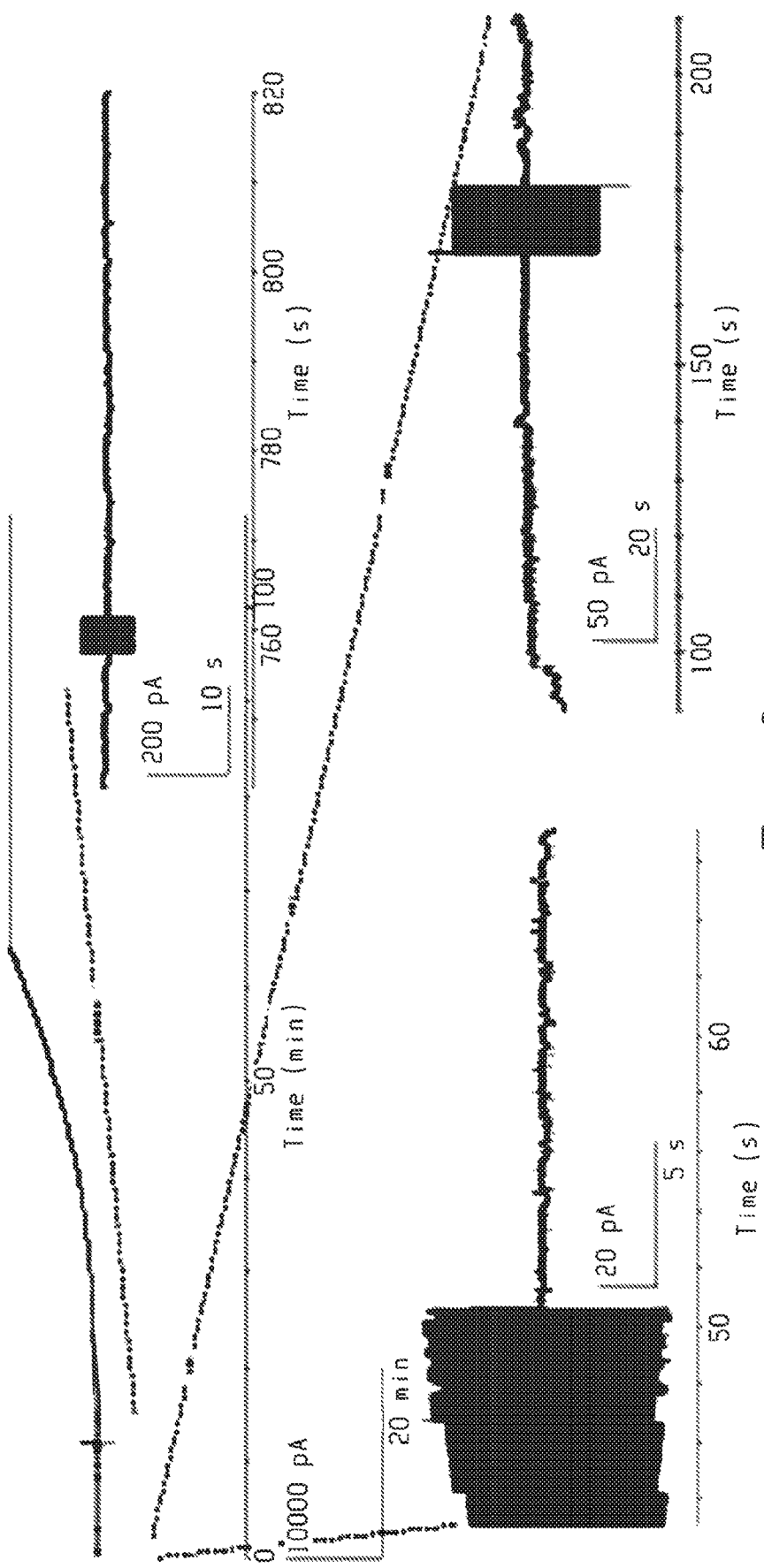
FIG. 9 presents graphs of electrophysiology recordings for a droplet interface bilayer, made by the rolling droplet approach in the presence of TBCP and a large number of pores incorporated into the bilayer (α-hemolysin concentrations approaching 1 mg/mL. In fact, pores inserted into the DIB until the conductance of the membrane exceeded the current capacity of the recording amplifier (at about 60 minutes, FIG. 9). Even though the current limit was reached, the DIB was still present for the entire recording as verified by visual inspection. Specifically, a ruptured DIB would coalesce into one droplet whereas a stable DIB will still be a pair of contacting droplets. A conventional lipid DIB membrane would typically have ruptured at the insertion of so many pores. Inset panels in FIG. 9 are expanded regions of the hour-long recording that show the reversible binding between cyclodextrin and hemolysin. These bindings are specific to hemolysin pores and do not occur at membrane defects. Thus, all conductance of the DIB was due to ions flowing through inserted hemolysin pores.

A polymer/lipid mixture of ratio 20:5:1 (DPhPC:DPhPE:TBCP) in chloroform was deposited on a glass surface, as described above, and dried. This was submerged in hexadecane and the droplets were rolled on its surface to pick up the material for monolayer formation. After several rolls, the droplets were suspended from the electrodes and brought into contact. Using this approach, stable DIBs containing IVTT were created and α-hemolysin activity was monitored as before (FIG. 8). Concentrations of hemolysin (up to 10 mg/mL) that would rupture a DIB with polymer incorporated by the method in which the polymer is present in the bulk oil bath (FIG. 9).

Figure 10:
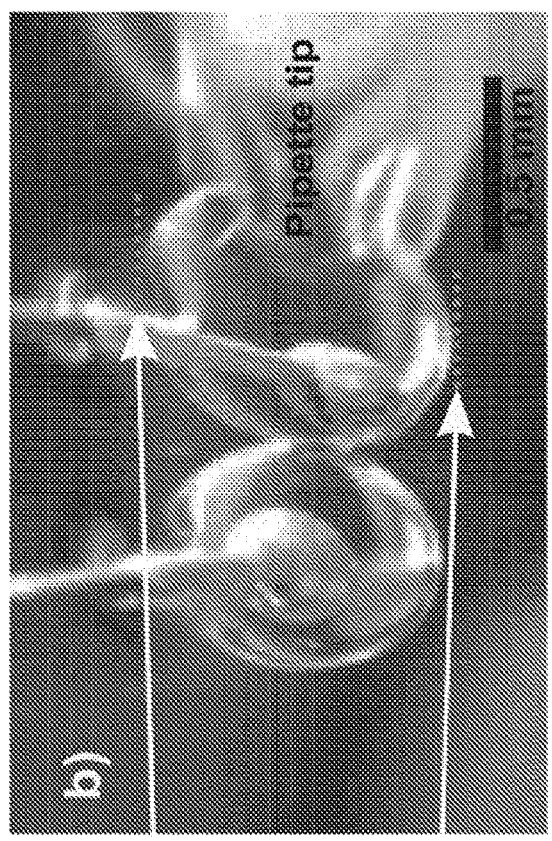
FIG. 10, panels a) and b) show the ability to inject a volume into a polymer-stabilized DIB.
Figure 10:
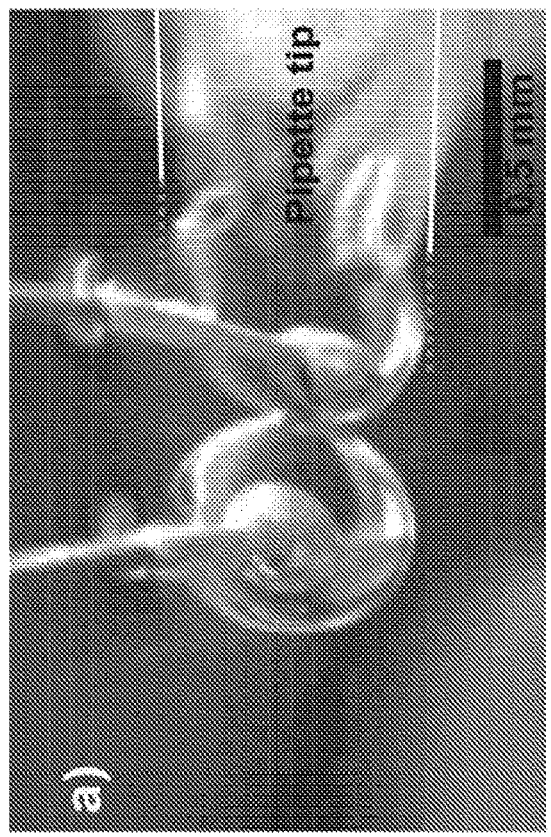

Having noted the wrinkles on the droplets and the extraordinary tolerance of polymer-stabilized DIBs made by the droplet-rolling method to IVTT and high toxin concentrations, we were curious to see whether these DIBs could withstand direct mechanical perturbations. Normally, a lipid-only DIB will coalesce if a volume is pumped into it. Thus, exchanging the contents of a DIB is a delicate operation. However, a DIB stabilized by TBCP using the droplet-rolling method withstood the injection and withdrawal of 0.5 μL by pipette (FIG. 10). Indeed, this process was repeated for three cycles without breaking the DIB as verified by subsequent electrical recording.

The compositions and methods disclosed herein include at least the following embodiments:

Embodiment 1

A pair of droplets in a hydrophobic medium comprising a first droplet of a first aqueous solution in the hydrophobic medium, the first droplet comprising a layer of amphipathic molecules around the surface of the first aqueous solution, and containing a transcription/translation extract and a heterologous polynucleotide encoding a membrane polypeptide; and a second droplet of a second aqueous solution in the hydrophobic medium, the second droplet comprising a layer of amphipathic molecules around the surface of the second aqueous solution; the first droplet and the second droplet being in contact with one another such that a bilayer of the amphipathic molecules is formed as an interface therebetween; an amphipathic polymer and optionally the encoded membrane polypeptide are inserted into the bilayer.

Embodiment 2

The pair of droplets of embodiment 1, wherein the membrane polypeptide is a channel or a pore.

Embodiment 3

The pair of droplets of embodiment 1 or 2, wherein the hydrophobic medium is oil.

Embodiment 4

The pair of droplets of embodiment 3, wherein the oil is a hydrocarbon oil, a silicone oil, a fluorocarbon oil, or a combination thereof.

Embodiment 5

The pair of droplets of any one of embodiments 1 to 4, wherein the amphipathic molecules are lipid molecules.

Embodiment 6

The pair of droplets of any one of embodiments 1 to 5, wherein each droplet has a volume of at least about 20 6 pL and less than about 1000 nL.

Embodiment 7

The pair of droplets of any one of embodiments 1 to 6, wherein the first or second droplet has a volume greater than or equal to 100 nL.

Embodiment 8

The pair of droplets of any one of embodiments 1 to 7, wherein the first or second droplet has a volume less than or equal to 800 nL.

Embodiment 9

The pair of droplets of any one of embodiments 1 to 8, wherein the polymer is a silicone.

Embodiment 10

The pair of droplets of embodiment 9, wherein the silicone is a polydimethysiloxane.

Embodiment 11

The pair of droplets of embodiment 10, wherein the silicone is a tri-block copolymer comprising a 65-mer of polydimethylsiloxane capped at both ends with a 6 mer of poly(2-methyl-2-oxazoline).

Embodiment 12

The pair of droplets of any one of the preceding embodiments, wherein the transcription/translation extract is a eukaryotic extract.

Embodiment 13

The pair of droplets of embodiment 12, wherein the eukaryotic extract is a HeLa cell extract.

Embodiment 14

The pair of droplets of any one of embodiments 1 to 13, wherein the bilayer of the amphipathic molecules has a diameter in the range from about 30 µm to about 1000 µm.

Embodiment 15

The pair of droplets of any one of embodiment 1 to 14, wherein the amphipathic molecules are the same or different in the two droplets.

Embodiment 16

The pair of droplets of any one of embodiment 1 to 15, wherein the first aqueous solution and the second aqueous solution are the same or different.

Embodiment 17

The pair of droplets of any one of embodiments 1 to 16, wherein the first or second droplet contains a test compound, a polypeptide, a polymer, or a combination thereof.

Embodiment 18

The pair of droplets of any one of embodiments 1 to 17, wherein the encoded membrane polypeptide is synthesized within the first droplet and inserted into the bilayer.

Embodiment 19

The pair of droplets of any one of embodiments 1 to 18, wherein the bilayer is stable for at least about 30 minutes.

Embodiment 20

The pair of droplets of any one of embodiments 1 to 19, wherein the concentration of the polymer in the hydrophobic medium is greater than about 0.05 g/L up to about 0.15 g/L.

Embodiment 21

The pair of droplets of any one of embodiments 1 to 20, wherein the polymer is present in the first or second aqueous solution.

Embodiment 22

The pair of droplets of any one of embodiments 1 to 21, wherein the membrane polypeptide is a eukaryotic polypeptide.

Embodiment 23

A system comprising a bilayer of amphipathic molecules provided at the interface between a first droplet of a first aqueous solution in a hydrophobic medium, the first droplet comprising a layer of amphipathic molecules around the surface of the first aqueous solution, and containing a transcription/translation extract and a heterologous polynucleotide encoding a membrane polypeptide; and a second droplet of a second aqueous solution in the hydrophobic medium, the second droplet comprising a layer of amphipathic molecules around the surface of the second aqueous solution; wherein the bilayer contains a polymer and a membrane polypeptide.

Embodiment 24

The system of embodiment 23, wherein the membrane polypeptide is a channel or a pore.

Embodiment 25

The system of embodiment 23 or 24, wherein the hydrophobic medium is oil.

Embodiment 26

The system of embodiment 25, wherein the oil is a hydrocarbon oil, a silicone oil, a fluorocarbon oil, or a combination thereof.

Embodiment 27

The pair of droplets of any one of embodiments 23 to 26, wherein the amphipathic molecules are lipid molecules.

Embodiment 28

The system of any one of embodiments 23 to 27, wherein each droplet has a volume of at least about 20 pL and less than about 1000 nL.

Embodiment 29

The system of any one of embodiments 23 to 28, wherein the first or second droplet has a volume greater than or equal to 100 nL.

Embodiment 30

The system of any one of embodiments 23 to 29, wherein the first or second droplet has a volume less than or equal to 800 nL.

Embodiment 31

The system of any one of embodiments 23 to 30, wherein the polymer is a silicone.

Embodiment 32

The system of embodiment 31, wherein the silicone is a polydimethysiloxane.

Embodiment 33

The system of embodiment 32, wherein the silicone is a tri-block copolymer comprising a 65-mer of polydimethylsiloxane capped at both ends with a 6 mer of poly(2-methyl-2-oxazoline).

Embodiment 34

The system of any one of embodiments 23 to 33, wherein the transcription/translation extract is a eukaryotic extract.

Embodiment 35

The system of embodiment 34, wherein the eukaryotic extract is a HeLa cell extract.

Embodiment 36

The system of any one of embodiments 23 to 35, wherein the bilayer of the amphipathic molecules has a diameter in the range from about 30 μm to about 1000 μm.

Embodiment 37

The system of any one of embodiment 23 to 36, wherein the amphipathic molecules are the same or different in the two droplets.

Embodiment 38

The system of any one of embodiment 23 to 37, wherein the first aqueous solution and the second aqueous solution are the same or different.

Embodiment 39

The system of any one of embodiments 23 to 38, wherein the first or second droplet contains a test compound, a polypeptide, a polymer, or a combination thereof.

Embodiment 40

The system of any one of embodiments 23 to 39, wherein the encoded membrane polypeptide is synthesized within the first droplet and inserted into the bilayer.

Embodiment 41

The system of any one of embodiments 23 to 40, wherein the bilayer is stable for at least about 30 minutes.

Embodiment 42

The system of any one of embodiments 23 to 41, wherein the concentration of the polymer in the hydrophobic medium is greater than about 0.05 g/L up to about 0.15 g/L.

Embodiment 43

The system of any one of embodiments 23 to 42, wherein the polymer is present in the first or second aqueous solution.

Embodiment 44

The system of any one of embodiments 23 to 43, wherein the membrane polypeptide is a eukaryotic polypeptide.

Embodiment 45

A method of forming a system comprising a bilayer of amphiphilic molecules provided at the interface between two droplets, comprising: forming a first droplet of a first aqueous solution in the hydrophobic medium, the first droplet comprising a layer of amphipathic molecules around the surface of the first aqueous solution, and containing a transcription/translation extract and a heterologous polynucleotide encoding a membrane polypeptide; forming a second droplet of a second aqueous solution in the hydrophobic medium, the second droplet comprising a layer of amphipathic molecules around the surface of the second aqueous solution; bringing the droplets into contact with one another in the hydrophobic medium so that a bilayer of the amphipathic molecules is formed as an interface between the contacting droplets; and incorporating a polymer into the bilayer.

Embodiment 46

The method of embodiment 45, further comprising incubating the first droplet under conditions such that the encoded membrane polypeptide is synthesized.

Embodiment 47

The method of embodiment 45 or 46, further comprising incubating the contacted droplets such that the membrane polypeptide is inserted into the bilayer.

Embodiment 48

The method of any one of embodiments 45 to 47, wherein the membrane polypeptide is a channel or a pore.

Embodiment 49

The method of any one of embodiments 45 to 48, wherein the membrane polypeptide is a eukaryotic membrane polypeptide.

Embodiment 50

The method of any one of embodiments 45 to 49, further comprising moving the droplets when the droplets are in contact with one another to vary the area of the bilayer of the amphipathic molecules.

Embodiment 51

The method of any one of embodiments 45 to 50, wherein the step of bringing droplets into contact with one another comprises moving one of the droplets into contact with the other droplet.

Embodiment 52

The method of embodiment 51, wherein the moved droplet is attached to an electrode.

Embodiment 53

The method of any one of embodiments 45 to 52, further comprising separating droplets which have been brought into contact with one another.

Embodiment 54

The method of any one of embodiments 45 to 53, wherein forming the first droplet or the second droplet comprises: (a) forming a droplet of aqueous solution in the hydrophobic medium; (b) before or after step (a), providing the amphipathic molecules in the hydrophobic medium; (c) after steps (a) and (b), incubating the droplet for a time sufficient for the layer of amphipathic molecules to form.

Embodiment 55

The method of any one of embodiments 45 to 53, wherein forming the first droplet or the second droplets comprises:

forming a droplet of aqueous solution containing the amphipathic molecules in the hydrophobic medium; and incubating the droplet for a time sufficient for the layer of amphipathic molecules to form.

Embodiment 56

A method of analyzing membrane polypeptide function, comprising contacting a test compound with the pair of droplets of any one of embodiments 1 to 22 or the system of any one of embodiments 23 to 45; and measuring a detectable signal from the system in the presence and in the absence of the test compound.

Embodiment 57

The method of embodiment 56, further comprising bringing electrodes into electrical contact with the droplets when the droplets are in contact with one another and measuring an electrical signal using the electrodes.

Embodiment 58

The method of embodiment 56, wherein the detectable signal is a signal from a chromophore.

Embodiment 59

The method of any one of embodiments 56 to 58, wherein the test compound is a small molecule or a polypeptide.

Embodiment 60

A droplet of aqueous solution in a hydrophobic medium, the droplet comprising a layer of amphipathic molecules around the surface of the aqueous solution, and containing a transcription/translation extract; and a heterologous polynucleotide encoding a membrane polypeptide and the hydrophobic medium or an aqueous phase containing a polymer capable of insertion into a bilayer of the amphipathic molecules.

Embodiment 61

The droplet of embodiment 60, wherein the membrane polypeptide is a channel or a pore.

Embodiment 62

The droplet of embodiment 60 or 61, wherein the hydrophobic medium is oil.

Embodiment 63

The droplet of embodiment 62, wherein the oil is a hydrocarbon oil, a silicone oil, a fluorocarbon oil, or a combination thereof.

Embodiment 64

The droplet of any one of embodiments 60 to 63, wherein the amphipathic molecules are lipid molecules.

Embodiment 65

The droplet of any one of embodiments 60 to 64, wherein the droplet has a volume of at least about 20 pL and less than about 1000 nL.

Embodiment 66

The droplet of any one of embodiments 60 to 65, wherein the droplet has a volume greater than or equal to 100 nL.

Embodiment 67

The droplet of any one of embodiments 60 to 66, wherein the droplet has a volume less than or equal to 800 nL.

Embodiment 68

The droplet of any one of embodiments 60 to 67, wherein the polymer is a silicone.

Embodiment 69

The droplet of embodiment 68, wherein the silicone is a polydimethysiloxane.

Embodiment 70

The droplet of embodiment 69, wherein the silicone is a tri-block copolymer comprising a 65-mer of polydimethylsiloxane capped at both ends with a 6 mer of poly(2-methyl-2-oxazoline).

Embodiment 71

The droplet of any one of embodiments 60 to 70, wherein the concentration of the polymer in the hydrophobic medium is greater than about 0.05 g/L up to about 0.15 g/L.

Embodiment 72

The droplet of any one of embodiments 60 to 71, wherein the aqueous phase containing the polymer is the aqueous solution within the droplet.

Embodiment 73

The droplet of any one of embodiments 60 to 72, wherein the transcription/translation extract is a eukaryotic extract.

Embodiment 74

The droplet of embodiment 73, wherein the eukaryotic extract is a HeLa cell extract.

Embodiment 75

The droplet of any one of embodiments 60 to 74, wherein the membrane polypeptide is a eukaryotic polypeptide.

Embodiment 76

The method of any one of embodiment 45 to 55, wherein incorporating a polymer into the bilayer comprises contacting the first or the second droplet with a lipid-polymer film on a surface of a substrate in the hydrophobic medium such that a lipid-polymer monolayer forms on a surface of the first or second droplet.

Embodiment 77

The method of embodiment 56, further comprising coating the substrate with a lipid-polymer solution to form the lipid-polymer film on the surface of the substrate.

Embodiment 78

The method of embodiment 56 or 57, wherein contacting the first or the second droplet with the lipid-polymer film occurs prior to bringing the droplets into contact with one another in the hydrophobic medium.

Embodiment 79

The method of any one of embodiments 56 to 58, wherein the lipid in the lipid-polymer film comprises 1,2-diphytanoyl-sn-glycero-3-phosphocholine (DPhPC), 1,2-diphytanoyl-sn-glycero-3-phosphoethanolamine (DPhPE), or a mixture thereof.

Embodiment 80

The method of any one of embodiments 57 to 59, wherein the lipid-polymer solution comprises a mass ratio of 1,2-diphytanoyl-sn-glycero-3-phosphocholine (DPhPC): 1,2-diphytanoyl-sn-glycero-3-phosphoethanolamine (DPhPE): polymer of 20:5:0.5 to 20:5:5, preferably the mass ratio is 20:5:1.

Embodiment 81

The method of any one of embodiments 45-55, wherein the hydrophobic medium or an aqueous phase contains the polymer and incorporating the polymer into the bilayer comprises the polymer self-inserting into the bilayer.

Embodiment 82

The method of any one of embodiments 45 to 61, wherein the polymer is a silicone.

Embodiment 83

The method of embodiment 62, wherein the silicone is a polydimethysiloxane.

Embodiment 84

The method of embodiment 63, wherein the silicone is a tri-block copolymer comprising a 65-mer of polydimethylsiloxane capped at both ends with a 6-mer of poly(2-methyl-2-oxazoline).

Embodiment 85

A system comprising a membrane separating first and second volumes of aqueous solution, the membrane comprising a lipid bilayer and an ion channel providing a passageway from one side of the membrane to the other, wherein the membrane contains 30% or less by weight of an amphiphilic polymer.

Embodiment 86

A system of embodiment 85 wherein the membrane comprises 0.1% to 10% by weight of the amphiphilic polymer.

Embodiment 87

The system of embodiments 85 or 86, wherein the amphiphilic polymer is a diblock or triblock copolymer.

Embodiment 88

A system of any of embodiments 85 to 87 wherein the first aqueous solution is a droplet in a hydrophobic medium, the droplet comprising a layer of lipid around its surface.

Embodiment 89

A system of embodiment 88 wherein the second aqueous solution is a droplet in a hydrophobic medium the droplet comprising a layer of lipid around its surface.

Embodiment 90

A system of embodiment 88 wherein the second aqueous solution is a hydrophilic layer.

Embodiment 91

A system according to any of the preceding embodiments wherein the first and second aqueous solutions each contain electrodes to provide a potential difference across the membrane.

Embodiment 92

A system according to any of the preceding embodiments wherein the first and/or second aqueous solutions comprise an electrolyte.

Embodiment 93

A system according to any of the preceding embodiments wherein the first and/or second aqueous solutions comprise a membrane destabilizing agent.

Embodiment 94

A system according to any of the preceding embodiments wherein the first and/or second aqueous solutions comprise a transcription/translation extract.

Embodiment 95

A system according to any of the preceding embodiments further comprising one of more droplets, each droplet comprising a layer of lipid around its surface and forming an interconnected droplet network, wherein a lipid bilayer is formed at each interface between droplets and wherein each lipid bilayer comprises an ion channel.

Embodiment 96

A system comprising a membrane separating first and second volumes of aqueous solution, the membrane comprising a lipid bilayer and an ion channel providing a passageway from one side of the membrane to the other, wherein the first and/or second volumes of aqueous solution comprise a lipid bilayer destabilizing agent wherein the membrane contains an amount of amphiphilic polymer effective for stabilization of the membrane.

Embodiment 97

A composition comprising a membrane comprising a lipid bilayer and an ion channel providing a passageway from one side of the membrane to the other, wherein the membrane contains 30% or less by weight of an amphiphilic polymer.

Embodiment 98

A composition comprises a pair of droplets in a hydrophobic medium, the pair of droplets comprises a first droplet of a first aqueous solution in the hydrophobic medium, the first droplet comprising a layer of lipid molecules around the surface of the first aqueous solution; and a second droplet of a second aqueous solution in the hydrophobic medium, the second droplet comprising a layer of lipid molecules around the surface of the second aqueous solution; the first droplet and the second droplet being in contact with one another such that a bilayer of the lipid molecules is formed as an interface therebetween; wherein the bilayer comprises an amount of amphipathic polymer effective for stabilization of the bilayer.

Embodiment 99

A composition comprising a droplet in a hydrophobic medium containing an aqueous solution and a hydrophilic layer, the droplet comprising a layer of lipid molecules around the surface of the first aqueous solution and the hydrophilic layer comprising a layer of lipid molecules on the surface of the second aqueous solution; the first droplet and the hydrophilic layer being in contact with one another such that a bilayer of the lipid molecules is formed as an interface therebetween; wherein the bilayer contains an amount of amphipathic polymer effective for stabilization of the bilayer.

Embodiment 100

A composition of embodiments 98 or 99 wherein the aqueous solution or the hydrophilic layer comprises a lipid bilayer destabilizing agent.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A system comprising
a bilayer of amphipathic molecules provided at the interface between
a first droplet of a first aqueous solution in a hydrophobic medium, the first droplet comprising a layer of amphipathic molecules around the surface of the first aqueous solution, and containing a eukaryotic transcription/translation extract and a heterologous polynucleotide encoding a membrane polypeptide; and
a second droplet of a second aqueous solution in the hydrophobic medium, the second droplet comprising a layer of amphipathic molecules around the surface of the second aqueous solution;
wherein the bilayer contains a polymer and the membrane polypeptide synthesized within the first droplet from the heterologous polynucleotide by the eukaryotic transcription/translation extract.

2. The system of claim 1, wherein the membrane polypeptide is a channel or a pore.

3. The system of claim 1, wherein the hydrophobic medium is oil.

4. The pair of droplets of claim 1, wherein the amphipathic molecules are lipid molecules.

5. The system of claim 1, wherein each droplet has a volume of at least about 20 pL and less than about 1000 nL.

6. The system of claim 1, wherein the polymer is a silicone.

7. The system of claim 1, wherein the first or second droplet contains a test compound, a polypeptide, a polymer, or a combination thereof.

8. The system of claim 1, wherein the bilayer is stable for at least about 30 minutes.

9. The system of claim 1, wherein the polymer is present in the first or second aqueous solution.

10. The system of claim 1, wherein the membrane polypeptide is a eukaryotic polypeptide.

* * * * *